(12) United States Patent
Genosar

(10) Patent No.: US 8,684,968 B2
(45) Date of Patent: Apr. 1, 2014

(54) HYPODERMIC DRUG DELIVERY RESERVOIR AND APPARATUS

(75) Inventor: Amir Genosar, Boulder, CO (US)

(73) Assignee: Aktivpak, Inc., Boulder, CO (US)

( * ) Notice: Subject to any disclaimer, the term of this patent is extended or adjusted under 35 U.S.C. 154(b) by 769 days.

(21) Appl. No.: 12/521,743

(22) PCT Filed: Dec. 27, 2007

(86) PCT No.: PCT/US2007/088918
§ 371 (c)(1),
(2), (4) Date: Jan. 4, 2010

(87) PCT Pub. No.: WO2008/083209
PCT Pub. Date: Jul. 10, 2008

(65) Prior Publication Data
US 2010/0179473 A1    Jul. 15, 2010

Related U.S. Application Data

(60) Provisional application No. 60/877,574, filed on Dec. 29, 2006, provisional application No. 60/904,397, filed on Mar. 2, 2007.

(51) Int. Cl.
*A61M 37/00* (2006.01)
(52) U.S. Cl.
USPC .......................................................... 604/132
(58) Field of Classification Search
USPC ........................................... 604/70, 132, 133
See application file for complete search history.

(56) References Cited

U.S. PATENT DOCUMENTS

| | | | |
|---|---|---|---|
| 2,743,724 A * | 5/1956 | Gispen | ........................ 604/237 |
| 2,794,437 A | 6/1957 | Tash | |
| 3,074,544 A | 1/1963 | Bolimeier et al. | |
| 3,315,801 A | 4/1967 | Lowry | |
| 3,387,609 A | 6/1968 | Shields | |
| 3,521,805 A | 7/1970 | Ward | |
| 3,554,256 A | 1/1971 | Anderson | |
| 3,608,709 A | 9/1971 | Pike | |
| 3,635,376 A | 1/1972 | Hellstrom | |
| 3,741,384 A | 6/1973 | Cloud | |

(Continued)

FOREIGN PATENT DOCUMENTS

| DE | 2647166 A1 | 5/1977 |
|---|---|---|
| DE | 2751078 A1 | 5/1979 |

(Continued)

OTHER PUBLICATIONS

International Searching Authority Notification of Transmittal of the International Search Report and the Written Opinion of the International Searching Authority, or the Declaration) dated Aug. 29, 2008.

(Continued)

*Primary Examiner* — Nicholas Lucchesi
*Assistant Examiner* — Diva K Chander
(74) *Attorney, Agent, or Firm* — Perkins Coie LLP

(57) ABSTRACT

A hypodermic drug delivery apparatus for delivering a pressurized medication fluid generally incorporates a reservoir containing at least one deliverable fluid, a reservoir pressurizing device, a rupturing member, a fluid administration device for communicating with the reservoir via a fluid passageway, and a rupture control mechanism for preventing rupture of a wall portion of the reservoir below a threshold pressure.

19 Claims, 17 Drawing Sheets

Figures 11b, 11c, 11d

(56) References Cited

U.S. PATENT DOCUMENTS

| | | | |
|---|---|---|---|
| 3,749,620 A | 7/1973 | Montgomery | |
| 3,847,279 A | 11/1974 | Montgomery | |
| 3,946,732 A | 3/1976 | Hursham | |
| 3,968,872 A | 7/1976 | Cavazza | |
| 3,986,640 A | 10/1976 | Redmond | |
| 4,011,949 A | 3/1977 | Braber et al. | |
| 4,020,836 A | 5/1977 | Cunningham | |
| 4,051,851 A * | 10/1977 | Tischlinger | 604/202 |
| 4,072,149 A | 2/1978 | Tischlinger | |
| 4,078,565 A | 3/1978 | Genese | |
| 4,084,588 A | 4/1978 | Koenig | |
| 4,084,718 A | 4/1978 | Wadsworth | |
| 4,140,409 A | 2/1979 | DeVries | |
| 4,236,652 A | 12/1980 | Beguhn | |
| 4,411,659 A | 10/1983 | Jensen et al. | |
| 4,430,013 A | 2/1984 | Kaufman | |
| 4,441,659 A | 4/1984 | Marklund | |
| 4,479,989 A | 10/1984 | Mahal | |
| 4,493,574 A | 1/1985 | Redmond et al. | |
| 4,548,601 A | 10/1985 | Lary | |
| 4,602,910 A | 7/1986 | Larkin | |
| 4,608,043 A | 8/1986 | Larkin | |
| 4,611,715 A | 9/1986 | Redmond | |
| 4,648,506 A | 3/1987 | Campbell | |
| 4,691,495 A | 9/1987 | Schuh | |
| 4,724,982 A | 2/1988 | Redmond | |
| 4,819,406 A | 4/1989 | Redmond | |
| 4,871,091 A | 10/1989 | Preziosi | |
| 4,955,871 A | 9/1990 | Thomas | |
| 4,961,495 A | 10/1990 | Yoshida et al. | |
| 5,029,718 A | 7/1991 | Rizzardi | |
| 5,131,760 A | 7/1992 | Farmer | |
| 5,176,634 A | 1/1993 | Smith et al. | |
| 5,241,150 A | 8/1993 | Garvey et al. | |
| 5,245,447 A | 9/1993 | Stemmle | |
| 5,287,961 A | 2/1994 | Herran | |
| 5,316,400 A | 5/1994 | Hoyt et al. | |
| 5,368,199 A | 11/1994 | Haas et al. | |
| 5,383,851 A | 1/1995 | McKinnon, Jr. et al. | |
| 5,395,031 A | 3/1995 | Redmond | |
| 5,425,447 A | 6/1995 | Farina | |
| 5,462,526 A | 10/1995 | Barney et al. | |
| 5,478,337 A | 12/1995 | Okamoto et al. | |
| 5,533,412 A | 7/1996 | Jerman et al. | |
| 5,543,097 A | 8/1996 | Fang | |
| 5,616,132 A * | 4/1997 | Newman | 604/185 |
| 5,637,087 A | 6/1997 | O'Neil et al. | |
| 5,681,291 A | 10/1997 | Galli | |
| 5,687,550 A | 11/1997 | Hansen et al. | |
| 5,716,343 A * | 2/1998 | Kriesel et al. | 604/132 |
| 5,836,922 A | 11/1998 | Hansen et al. | |
| RE35,986 E | 12/1998 | Ritson et al. | |
| 5,848,991 A * | 12/1998 | Gross et al. | 604/140 |
| 5,884,759 A | 3/1999 | Gueret | |
| 5,921,962 A * | 7/1999 | Kriesel et al. | 604/132 |
| 5,957,895 A | 9/1999 | Sage et al. | |
| 6,007,264 A | 12/1999 | Koptis | |
| 6,017,598 A | 1/2000 | Kreischer et al. | |
| 6,041,930 A | 3/2000 | Cockburn | |
| 6,045,534 A | 4/2000 | Jacobsen et al. | |
| 6,085,942 A | 7/2000 | Redmond | |
| 6,086,562 A | 7/2000 | Jacobsen et al. | |
| 6,148,996 A | 11/2000 | Morini | |
| 6,171,285 B1 | 1/2001 | Johnson | |
| 6,203,535 B1 | 3/2001 | Barney et al. | |
| 6,245,056 B1 | 6/2001 | Walker et al. | |
| 6,258,063 B1 * | 7/2001 | Haar et al. | 604/141 |
| 6,354,603 B1 | 3/2002 | Villette | |
| 6,435,341 B1 | 8/2002 | Nobbio | |
| 6,530,900 B1 | 3/2003 | Daily et al. | |
| 6,656,147 B1 | 12/2003 | Gertsek et al. | |
| 6,675,660 B1 | 1/2004 | Mosier et al. | |
| 6,743,211 B1 | 6/2004 | Prausnitz et al. | |
| 6,780,171 B2 | 8/2004 | Gabel et al. | |
| 6,805,998 B2 | 10/2004 | Jenson et al. | |
| 6,906,436 B2 | 6/2005 | Jenson et al. | |
| 6,924,164 B2 | 8/2005 | Jenson | |
| 6,979,316 B1 | 12/2005 | Rubin et al. | |
| 6,996,951 B2 | 2/2006 | Smith et al. | |
| 7,004,213 B2 | 2/2006 | Hansen | |
| 7,011,650 B2 | 3/2006 | Rosoff et al. | |
| 7,025,200 B2 | 4/2006 | Fontana | |
| 7,115,108 B2 | 10/2006 | Wilkinson et al. | |
| 7,121,409 B1 | 10/2006 | Hamilton et al. | |
| 7,192,549 B2 | 3/2007 | Hansen | |
| 7,225,683 B2 | 6/2007 | Harnett et al. | |
| 7,407,493 B2 | 8/2008 | Cane' | |
| 7,416,540 B2 | 8/2008 | Edwards et al. | |
| 7,464,811 B2 | 12/2008 | Patterson et al. | |
| 2001/0047162 A1 | 11/2001 | Yugari | |
| 2002/0123740 A1 | 9/2002 | Flaherty et al. | |
| 2003/0080129 A1 | 5/2003 | Takimoto et al. | |
| 2004/0240324 A1 | 12/2004 | Isbitsky et al. | |
| 2004/0249339 A1 | 12/2004 | Willis et al. | |
| 2005/0004514 A1 | 1/2005 | Hochman | |
| 2006/0079862 A1 | 4/2006 | Genosar | |
| 2006/0276755 A1 | 12/2006 | Sullivan et al. | |
| 2006/0283727 A1 | 12/2006 | Nelson et al. | |
| 2007/0144923 A1 | 6/2007 | Houwaert et al. | |
| 2007/0299391 A1 | 12/2007 | Yoshikawa et al. | |
| 2008/0177244 A1 | 7/2008 | Capitaine et al. | |
| 2008/0249499 A1 | 10/2008 | Vancaillie et al. | |
| 2008/0300570 A1 | 12/2008 | Fowles et al. | |
| 2010/0179473 A1 * | 7/2010 | Genosar | 604/70 |

FOREIGN PATENT DOCUMENTS

| | | |
|---|---|---|
| DE | 4203430 A1 | 8/1993 |
| DE | 100 32 937 A1 | 1/2001 |
| EP | 0088730 A1 | 9/1983 |
| EP | 0088731 A1 | 9/1983 |
| EP | 0370571 | 10/1993 |
| EP | 1 201 233 | 5/2002 |
| EP | 1201233 A1 | 5/2002 |
| FR | 1065305 A | 5/1954 |
| FR | 1121237 | 7/1956 |
| FR | 2633519 A1 | 1/1990 |
| GB | 697643 | 9/1953 |
| GB | 770341 | 3/1957 |
| GB | 770341 A | 3/1957 |
| WO | 92/20595 A1 | 11/1992 |
| WO | 97/06073 A1 | 2/1997 |
| WO | 01/78806 A1 | 10/2001 |
| WO | 02/05889 A1 | 1/2002 |
| WO | 2005/002649 A1 | 1/2005 |
| WO | 2007/068032 A1 | 6/2007 |

OTHER PUBLICATIONS

International Searching Authority "Notification of Transmittal of the International Search Report and the Written Opinion of the International Searching Authority, or the Declaration" Mar. 10, 2009.

Written Opinion of the International Searching Authority for PCT/US07/88918 mailed Aug. 29, 2008.

International Preliminary Report on Patentability for PCT/US07/88918 mailed Jun. 30, 2009.

Documents printed from www.rommelag.com, 4 pages printed on Jan. 25, 2010.

Documents printed from www.weiler-bfs.com, 10 pages printed on Jan. 25, 2010.

Documents printed from www.sarong.it, 7 pages printed on Jan. 25, 2010.

Documents printed from www.lameplast.it, 15 pages printed on Jan. 25, 2010.

Documents printed from www.sanner.de, 5 pages printed on Jan. 25, 2010.

Documents printed from www.justformen.com, 1 page printed on Jan. 27, 2010.

Documents printed from www.unfill.it, 14 pages printed on Jan. 28, 2010.

Documents printed from www.bioject.com, 6 pages printed on Jan. 28, 2010.

(56) References Cited

OTHER PUBLICATIONS

Documents printed from www.injex.com, 6 pages printed on Jan. 28, 2010.
Documents printed from www.mediject.com, 2 pages printed on Jan. 28, 2010.
Documents printed from www.zogenix.com, 2 pages printed on Jan. 28, 2010.
Documents printed from www.valeritas.com, 1 page printed on Jan. 28, 2010.
Documents printed from www.crossject.com, 1 page printed on Jan. 28, 2010.
Documents printed from www.penjet.com, 1 page printed on Jan. 28, 2010.

* cited by examiner

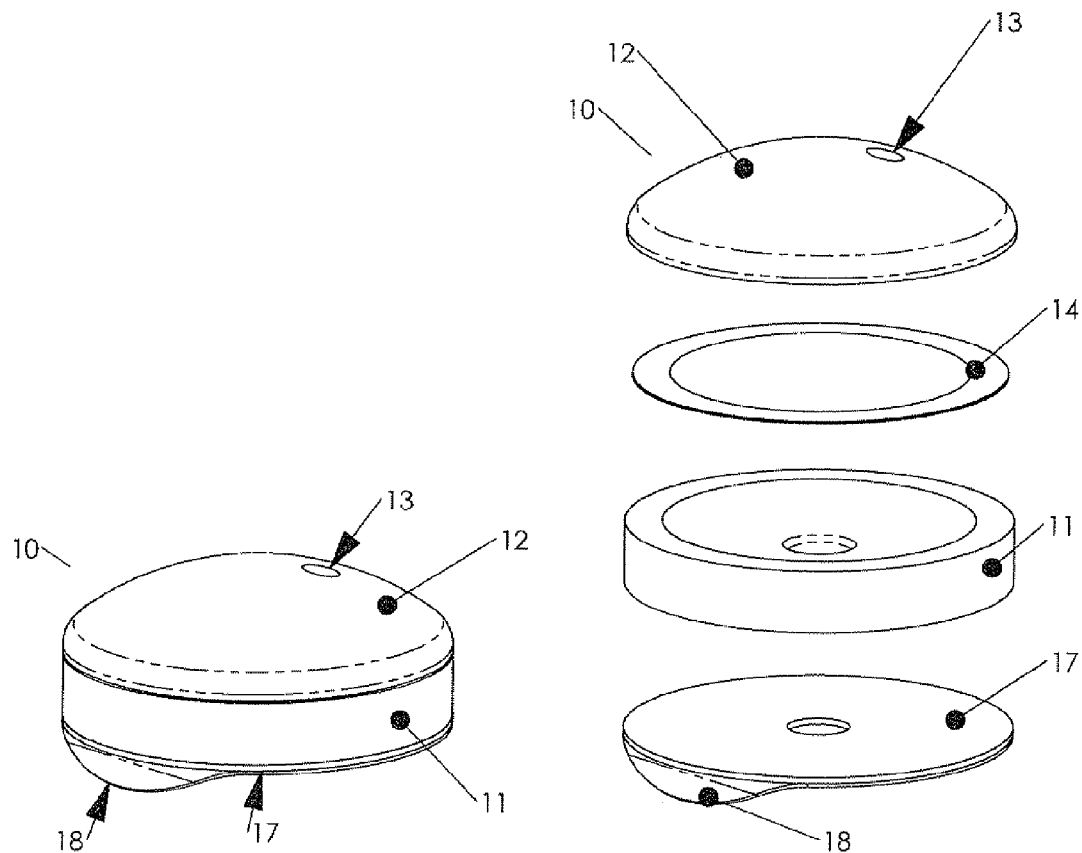
Figure 1a
Figure 1b
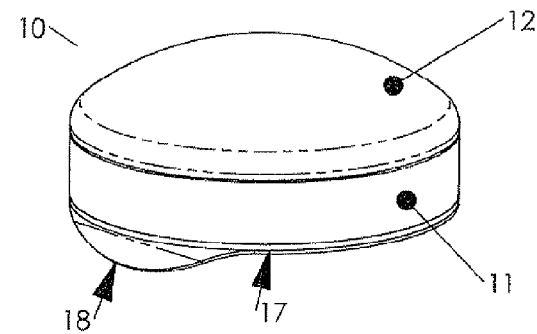
Figure 1c

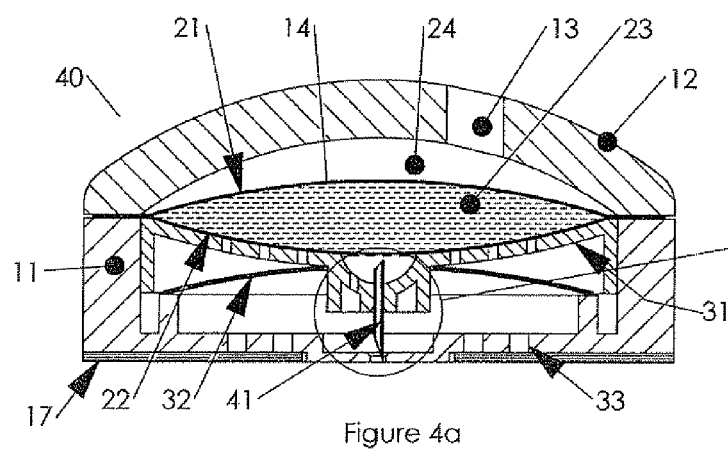
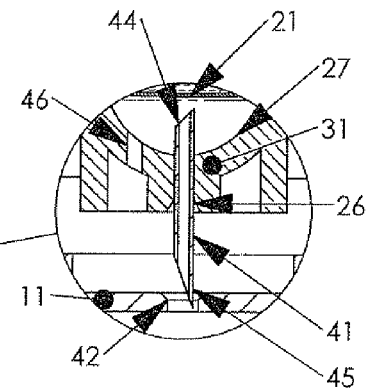
Figure 4a
Figure 4b
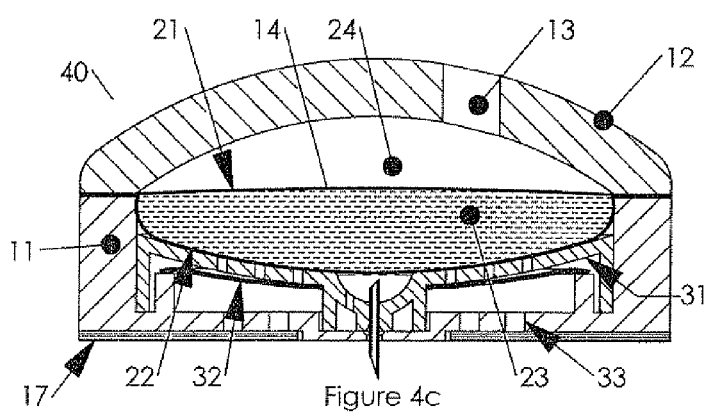
Figure 4c
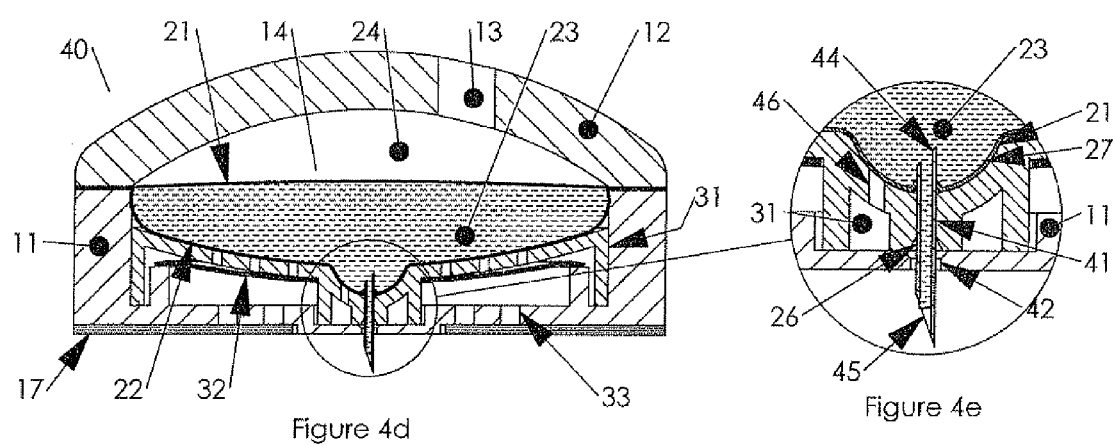
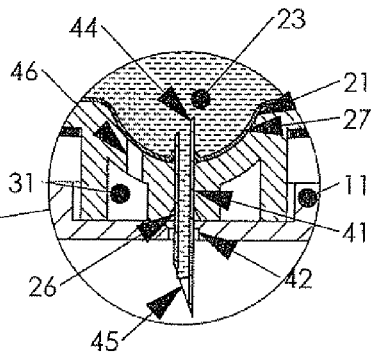
Figure 4d
Figure 4e

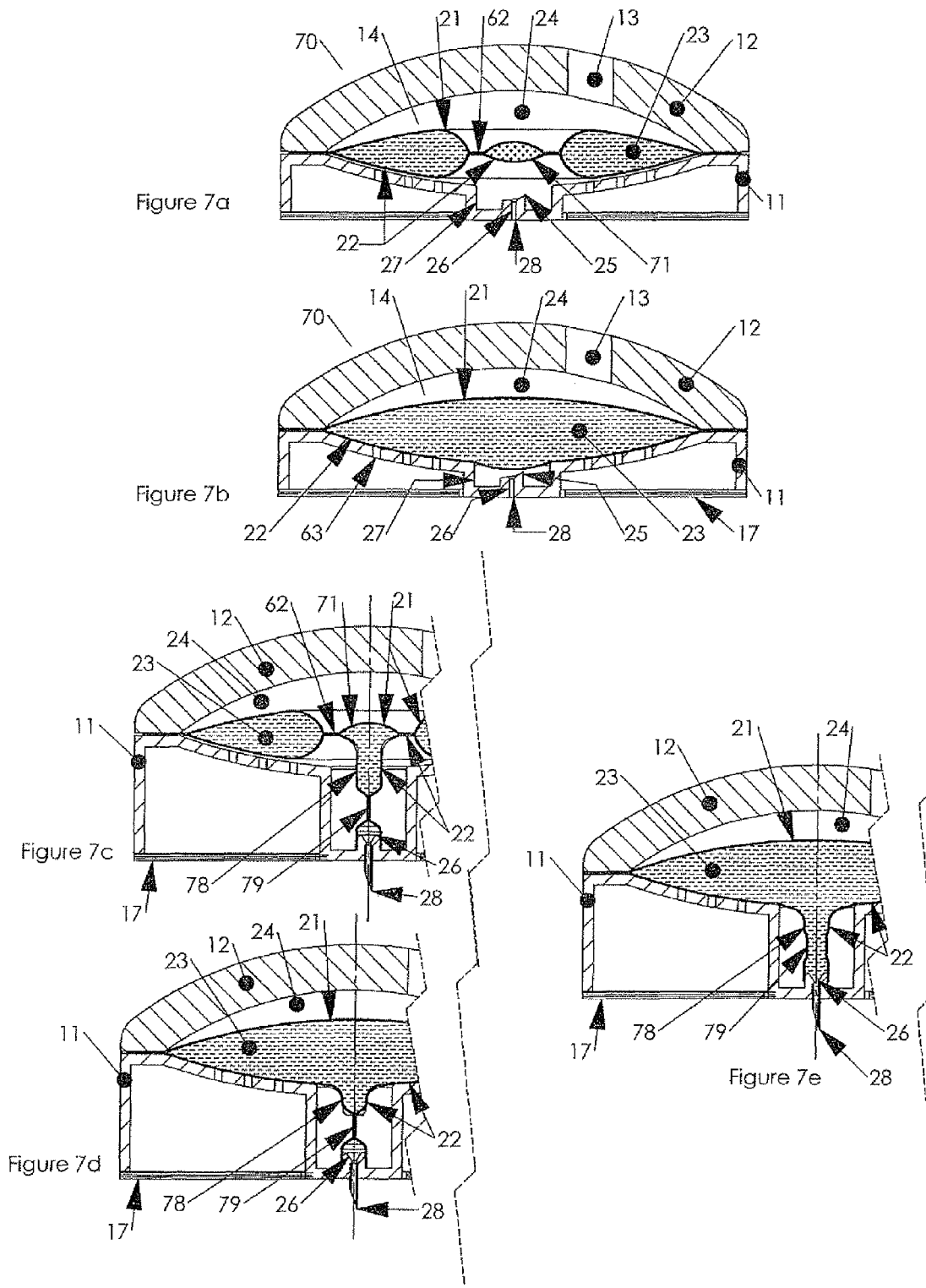

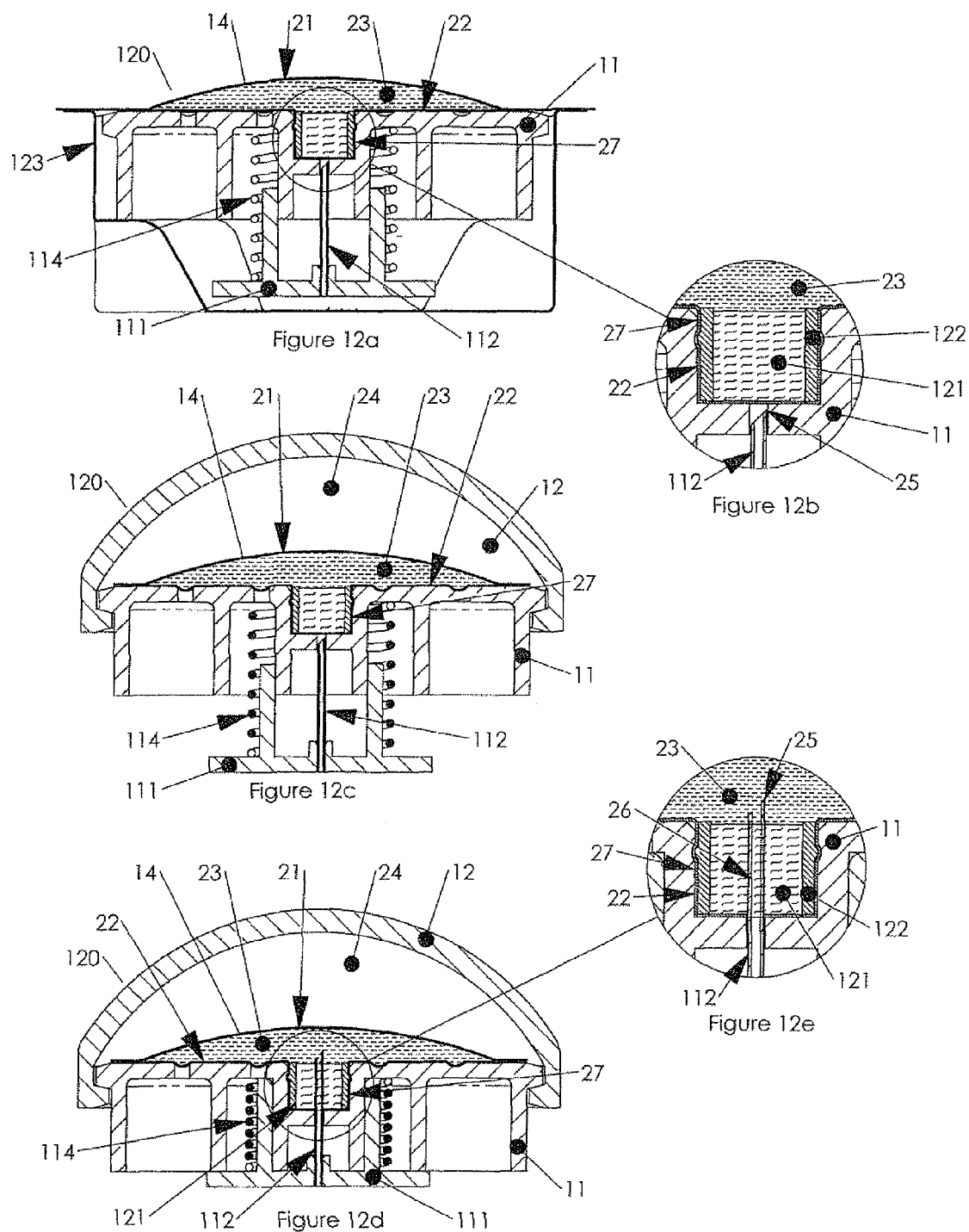

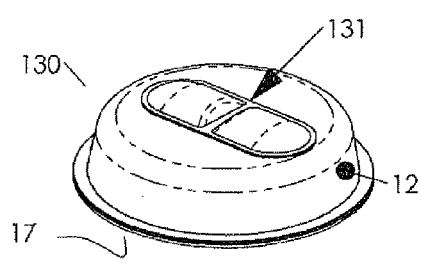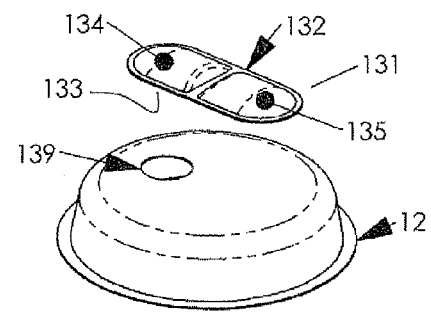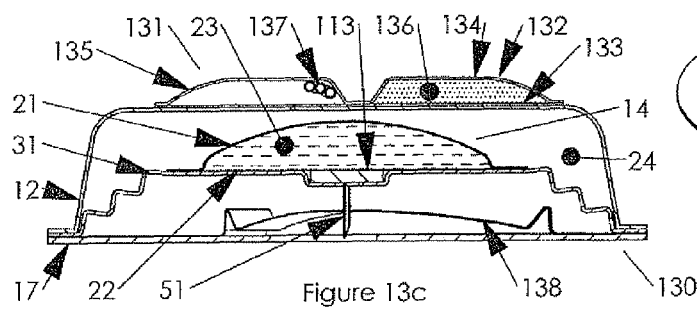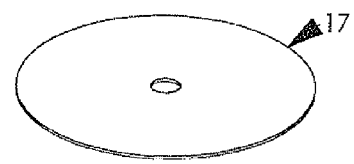
Figure 13a
Figure 13b
Figure 13c
Figure 13d

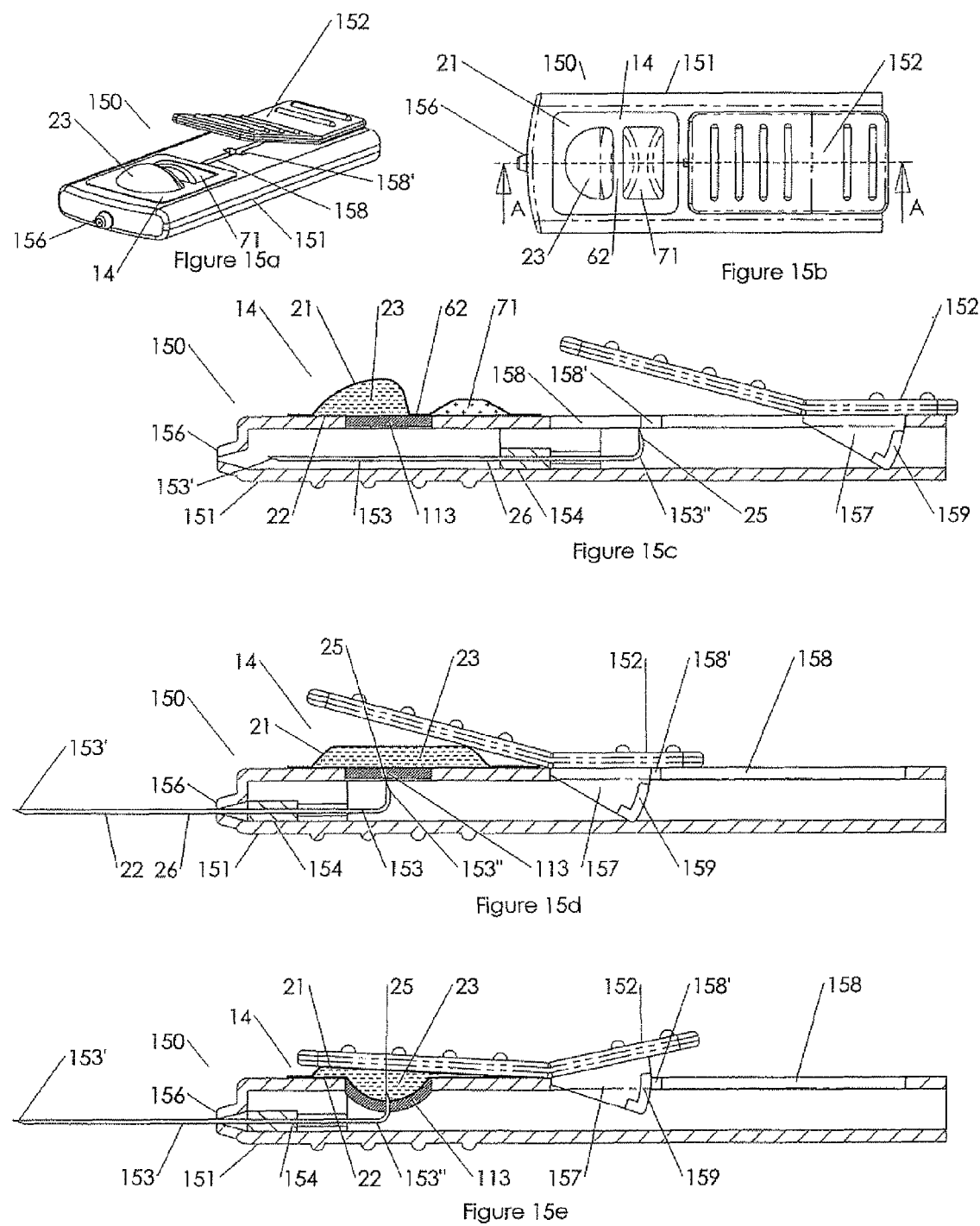

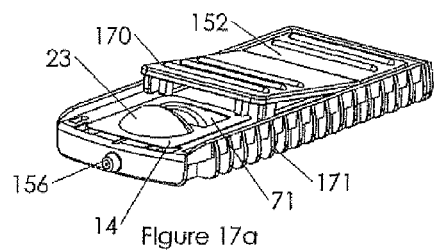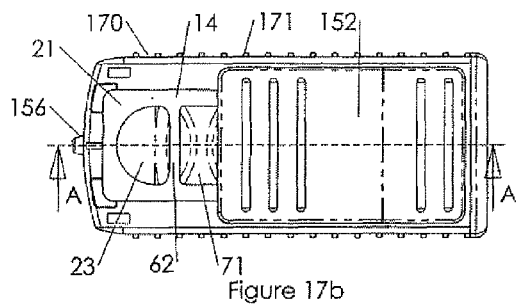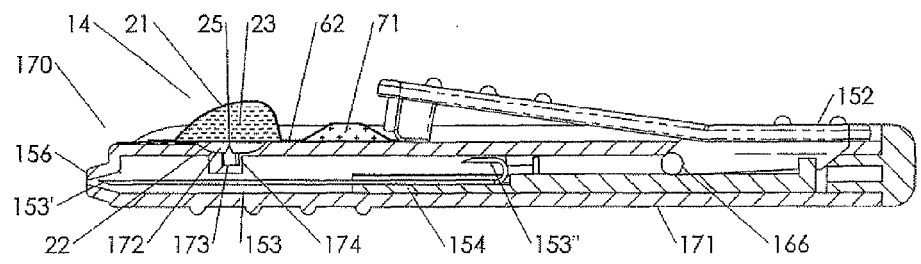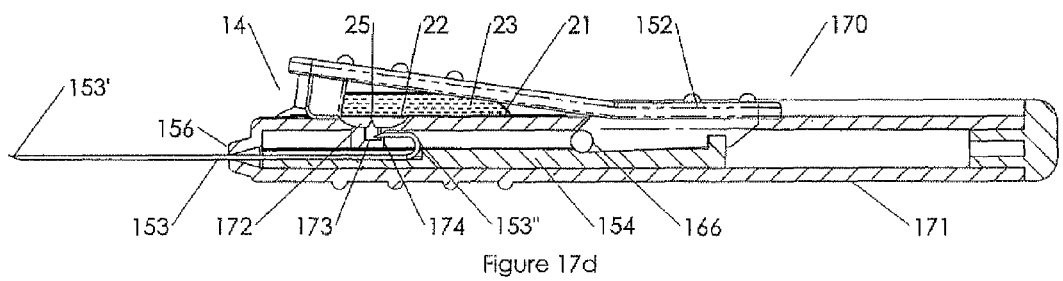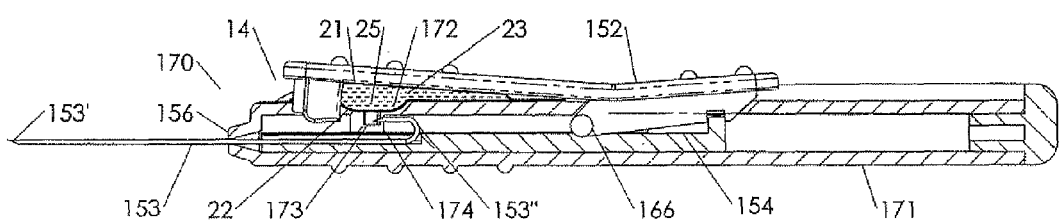
Figure 17a
Figure 17b
Figure 17c
Figure 17d
Figure 17e

HYPODERMIC DRUG DELIVERY RESERVOIR AND APPARATUS

BACKGROUND OF THE INVENTION

1. Field of the Invention

This invention related to a method and apparatus for storing and delivering drugs. More particular this invention relates to a method and apparatus where the drug is stored in, and delivered from, a pouch that is pressurized before delivery.

2. Discussion of the Background

Drug delivery technologies are becoming a critical part of the entire drug development process. Pharmaceutical companies are realizing the importance of drug delivery in the initial stages of drug development. The novel formulation of a drug by application of delivery technologies has opened many doors for the patients, physicians, as well as pharmaceutical companies. Moreover, drug delivery companies can offer new life to older drugs so that the drug can continue to generate more revenues for the pharmaceutical and biotechnology companies. New delivery methods also extend the product life of drugs going off patent, thus delaying the entry of generics in the market.

Drug delivery technologies are being used to not only improve pharmacokinetic and pharmacodynamic profiles, but are also being targeted to improve patient comfort and compliance. Targeted delivery of drugs is also being leveraged to reduce side effects of a number of drugs. In addition to pharmaceutical products, a number of biotechnology products are being developed that require an alternate or novel route of administration because most of them are ineffective when administered orally. An effective delivery system is thus targeted to improve the performance of both new and old drugs.

One aspect of the above said is the form of packaging and storing the drug/apparatus yet keeping a simple and convenient fashion to operate the administration procedure. In several cases the apparatus structure does not comply with the requirements for storage and transportation of the drug to the point and time of use. For example molded plastic parts are permeable to several liquid form substances and in various cases where the drug reservoir of the apparatus is made from molded plastic components the drug is introduced into the apparatus just prior to the treatment, making the administration process more sophisticated and in many cases more expensive. Other drugs are advantageously be compounded just prior to the treatment in order to extend the drug's shelf life and durability to environmental conditions between the time of manufacturing and the time of administration. This is in particularly true to biological substances such as vaccines which are advantageously kept in a powder form and reconstituting in a liquid form just prior to administration.

Pouches made of thin films or foils are advantageous for drug storage (vs. injection molded or blow molded containers) as they can be constructed from drug compatible materials with excellent barrier properties and enhanced chemical stability. In particular multilayer films and foils, co-extruded or laminated, can combine properties which provide comprehensive packaging solution including, good bonding/sealing properties, strength, chemical resistance, gas and liquids barrier, and UV and other sorts of radiation resistance.

Hypodermic injection is meant to include intra-dermal, subcutaneous and intra-muscular injections.

The invasiveness and fear of injections (resulting in poor patient compliance) as well as a financial incentive to gain valuable market share has encouraged a number of companies to develop technologies that can lead to needle-free delivery of medications. Needle-free injection devices propel a small jet of liquid or powder at high speed, causing it to penetrate the skin for subcutaneous, intradermal, or intramuscular administration. These devices have been used for mass vaccinations for a number of years; however, only recently are they being promoted as devices for the self-administration of parenteral drugs. Improvement in technology, increased development of formulations for needle-free delivery, and reduced prices are expected to spur the acceptance of and demand for needle-free devices in the coming years.

One of the forms of injectable delivery, needle-free technologies, provides an alternative to needles normally associated with injectables delivery. Needle-free injectors are devices that do not use a needle to administer medication. The mechanism involves high pressure to push the medication through the skin to the desired penetration site. Using pressure instead of the needle allows for a non-invasive method of drug delivery. Pressure is produced by using either a gas (carbon dioxide or nitrogen) or a spring device. The pressure forces the medication through a small opening in the device while it is held against the skin. This creates a fine stream of the medication that penetrates the skin. There are a few devices on the market that are spring powered, however, most are gas powered. The penetration depth of the drug is dependent upon the amount of pressure used. Devices currently on the market administer the drug to the subcutaneous, intradermal, and intramuscular tissues, together referred to as hypodermic administration.

Currently, the applications of the device are for delivering insulin, vaccines, growth hormones, and other medications. Applying the device to deliver proteins and peptides is in the initial stages of development. Some of the major companies operating in the needle-free delivery markets include Bioject, Injex (formerly Equidyne), Antares, BioValve, Crossject, PenJet, and Aradigm. Of course there are other companies, but the following is to provide readers with a brief review on some of the technologies available in needle-free devices and what makes them unique from each other.

The Biojector 2000, from BioJect has the ability to deliver both intramuscular and subcutaneous injections up to 1 ml. Vaccines and medications can be delivered using this device. It was designed to be used in professional settings, delivering multiple injections. This system has three components: injection device, disposable needle-free syringe, and a CO2 cartridge. Each CO2 cartridge can deliver between 10 and 15 injections before having to be replaced.

Vitajet 3:

The Vitajet is currently used to deliver 0.02 to 0.50 ml. The device has three components: the reusable injection device, disposable Crystal Check nozzle, and disposable vial holder. The nozzle is replaced once a week. It may be used in the home for self-administration. The Vitajet 3 is powered by an internal spring. More than 3,000 injections may be delivered from single device.

Iject:

Currently in development, the Iject has the ability to deliver medication subcutaneously, intramuscularly, and intradermally. It may be set on various injection volumes. This device is gas powered and may be available either as a pre-filled single-use disposable system or a reusable device. The reusable version uses pre-filled cartridges of medication that are replaced.

Injex 30:

The Injex 30 delivers medication to the subcutaneous tissue. Delivering from 0.05 to 0.30 ml, the Injex 30 consists of a main body, a trigger release, and a dual safety system. A safety system helps to prevent accidental discharge. The system is made of stainless steel to be durable.

Injex 50:

Injex 50 is designed for frequent use and has the ability to deliver larger dosage amounts from 0.10 to 0.50 ml per injection.

Jet Syringe:

Currently in development stages, the Jet Syringe is a single-use disposable needle-free injection device that is powered by a spring mechanism. Advantages of the device are its small design and convenience of attaching a pharmaceutical pre-filled ampule. The Jet Syringe, which can deliver up to 0.5 ml, can be configured with an adjustable dose fillable ampule or a proprietary prefilled glass ampule for fixed-dose applications. A general use 510(k) clearance has been granted for administration of subcutaneous injections. The prefilled version is also ideal for subcutaneous vaccines.

Antares Medi-Jector Vision:

Antares' Medi-Jector Vision is a small, handheld device that delivers to the subcutaneous tissue. The device is targeted for delivery of insulin for not only adults but also children, and is compatible with all brands of U-100 insulin. The Medi-Jector Vision uses pressure to create a micro-thin stream of insulin that penetrates the skin and is deposited into the subcutaneous (fatty) tissue in a fraction of a second.

Aradigm Intraject:

The Intraject is expected to enter the market in the next couple of years. Intraject is composed of two main parts: the glass capsule with a pre-filled volume of 0.5 ml, and a compact nitrogen gas power source ("the actuator"). To use Intraject, the patient snaps off the plastic tip (which acts as a sterile seal), removes the safety band, and presses the device against an area of the skin to activate delivery. The delivery process is completed in less than 60 milliseconds. Formulations delivered via Intraject are usually identical to those delivered via conventional subcutaneous injection, allowing for an abbreviated bioequivalence-based clinical and regulatory pathway. Since the drug-containing capsule is made of glass, existing stability in glass ampules can also be used to support Intraject filings.

BioValve Miniject:

Biovalve's Mini-Ject needle-free system is designed to deliver a wide range of drugs, ranging from small molecules to large proteins, fragile antibodies, and vaccines. The small, convenient, and disposable device can be targeted to deliver via intradermal, subcutaneous, or intramuscular routes. Miniject's propulsion technology includes a multi-phased energy system that can deliver from 0.1- to 1.3-ml drug volumes. Mini-Ject's orifice is manufactured using a proprietary process to ensure exit taper and orifice alignment, resulting in minimal turbulence and improved performance. The device, which is filled on a standard pharmaceutical line, can be configured to deliver solutions, for which it has a single part, solution-stable, prefilled cartridge. It is also designed for the delivery of lyophilized formulations, for which it has a dual-stage cartridge.

Crossject:

The device is a single-use pre-filled needle-free injection targeted for subcutaneous, intramuscular, or intradermal use. Based on novel gas generator technology, Crossject can deliver drug volumes from 0.2 to 1 ml in few hundreds of a second. The company, which likens the gas-generation reaction to that used in car airbags, points out that there is no pressurized gas present while the injector is kept in storage, thus avoiding the difficulties of gas leakage. The gas generator contains the chemical energy source and is triggered by the impact of a spring on the reactive materials. The drug container is composed of a glass tube (type I borosilicate) capped at both ends by elastomer corks. The third module, the nozzle, is manufactured from polycarbonate and can contain one or more orifices depending on the quantity and viscosity of the formulation. The orifices are 100 to 300 μm in diameter. CrossJect cites close control over the gas pressure profile as one of the advantages of its device over pressurized gas- and spring-propelled systems. This enables the injection profile to be optimized and the precise depth of injection to be determined.

PenJet:

The device is a small needle-less, disposable jet injector that delivers a single dose of medication using nitrogen gas canisters. PenJet can deliver both liquid and lyophilized drugs with volumes ranging from 0.1 to 0.5 ml. PenJet is powered by self-contained compressed inert gas and is either shipped prefilled with a drug or filled prior to delivering a needle-less injection. Ease of operation and low cost make PenJet applicable for usages ranging from mass inoculations of entire populations to home delivery of pharmaceuticals by patients or their caregivers. They are available for needle-less subcutaneous, intradermal, and some intramuscular injections.

Several disadvantages exist with the above mentioned devices and their technology including:

1. All of the above devices and technologies utilize a drug reservoir in a fashion of a cylinder and a piston. This construction present sealing challenges between the drug cylinder and piston as well as friction issues.

2. The activation mechanisms are either gas loaded piston or spring loaded arrangement which are complex and expensive to manufacture. It would be advantageous if the gas pressure could be applied directly to the drug reservoir avoiding redundancy of mechanisms.

3. In the spring loaded devices the loading mechanisms are cumbersome to operate. This disadvantage becomes more pronounced where massive administration has to be conducted for example in a massive vaccination campaign.

4. For those devices that comprise a prefilled reservoir, said reservoir is usually made from glass and it is expensive to manufacture.

5. Other devices utilize reservoirs comprising molded plastic walls, which are not suitable for storing and transportation of the drugs. In this case the administration procedure requires filling the device prior to use, making the procedure cumbersome and in certain devices a contamination risk.

6. Moreover all of the above devices require a potential energy storage or generation means capable of instantly pressurizing the drug reservoir. That requirement limits the choice of adequate solutions to relatively expensive ones or sophisticated to operate solutions.

7. The above prior art needle free devices require extremely high pressure (about 300 bar) to initially penetrate the skin which impose extreme mechanical requirements on the components of these devices.

8. And lastly, none of the above devices is inherently adequate for combination-drug administration, or drug reconstitution (resuscitation), where content of separately sealed reservoirs are to be expelled in a single administration, as these device simply dispense the solution that present in its piston fashion reservoirs.

The above listed disadvantages are partly addressed where the piston/cylinder fashion drug reservoir is replaced by a collapsible reservoir. In the prior art there are also known devices for a needle-free injection of liquids which avoid stoppers or the like. European patent application 0 370 571 describes a system where an ampule which contains a liquid medication is being mechanically compressed by a rod. This compression drives the liquid medication through one or more orifices to generate a liquid jet. While this apparatus mostly avoids the problems associated with frictional surfaces and stoppers moving in a cylinder this apparatus has a drawback that the flexible part of the ampule may be destroyed when pressed by the rod. A further drawback of this device is that the pressures which can be applied to the ampule are limited due to the risk of destruction and also by the relatively low energy stored in a spring. Another disadvantage of this apparatus is that a mechanical compression of the ampule by a rod cannot guarantee that the liquid within the ampule is being ejected totally. Such a device is therefore insufficient when it is desired to inject a specific amount of medication.

In FR-1.121.237 there is described a device for the hypodermic injection of liquids using a high pressurized liquid jet. The device comprises a compressible container for liquid medication which is attached to a unit having a fluid channel. The unit with the fluid channel is connected to a unit with a nozzle so that a continuous channel is being formed through which the liquid medication can be expelled. For a hypodermic injection the unit with the channel is placed on a mounting element so that the medication container is surrounded by a chamber and pressure is applied to said chamber by ignition of an explosive. The document FR-1.121.237 teaches that the medication container and the unit with the channel are combined by the user. The user fills the liquid to be injected into the medication container and tightly closes the medication container by screwing on the unit with the fluid channel. Such a process is not only cumbersome but it also bears the risk that the medication and/or the fluid channel is contaminated. The injection of a contaminated medical fluid is totally unacceptable in the therapeutic field. This problem of contamination is mostly unresolved in the prior art of hypodermic liquid injection. Furthermore the FR-1.121.237 does not give any information regarding the pressure of the liquid jet and how this pressure can be controlled to be in a specific range or how the pressure can be changed by the user to comply with his specific needs. A further drawback of the system described in FR-1.121.237 is that no means for purging air from the liquid chamber are described. However, air within the liquid chamber leads to disadvantageous effects as described further below.

Reference GB-697,643 describes a device for hypodermic injections using a flexible or collapsible element which is being compressed. The device described in this document is very complicated and uses a rechargeable pressure chamber into which a pressurized gas is introduced and in addition thereto a chamber with a hydraulic fluid is employed. With this device it is possible to control the pressure by which the liquid is being expelled from the container. However, a flexible container is needed into which the collapsible medication container is being introduced. From the function of this device it must be assumed that it is impossible to expel all of the fluid which is within the medication container. The document GB-697,643 further discloses a medication container which is sealed and can be used to store a medication under sterile conditions. However, this document does not disclose a medication container including a sterile nozzle. Therefore this document does not give an overall solution to the object of sterile injection.

U.S. Pat. Nos. 3,387,609, and 4,051,851 describe a prefilled disposable hypodermic syringe having a diaphragm, made from a resilient and penetrable material, at the dispensing end of a medicament vial, preventing the fluid connection between said medicament and the administration mean of the device. A rupturing member positioned in proximity to said diaphragm such that, upon presence of pressure in the vial said diaphragm collapse toward the rupturing member at which point the diaphragm is ruptured establishing a fluid communication between the vial and the administration means. Several other patents (referring to the above patents (including U.S. Pat. Nos. 4,0551,851; 4,072,149; 4,084,718; 6,354,603) repeat the fundamental idea of rupturing a sealed medicament reservoir in similar fashions and suffer from a common drawback, and incompetence with the device of the present invention. While U.S. Pat. Nos. 3,387,609 and 4,051, 851 describes a rupturable reservoir one may understand that the rupturing is desired immediately upon performing the injection, and that excessive pressure built in the vial prior to the rupture of the diaphragm works against the purpose of the idea. Therefore the rupturing mechanism of the present invention is incompetence for controlling the drug administration pressure. It is also noted that the integrity of the prefilled package is not established and that the sealing of the medicament is limited.

The disadvantages listed above for the devices using collapsible reservoir are addressed by U.S. Pat. No. 6,258,063 which describes A hypodermic injection system allows for the generation of a high pressure liquid jet capable of passing through the skin. The system uses two regions, the first region being flexible or squeezable and the second region having at least one exiting orifice through which the liquid jet can be expelled. The flexible region can be deformed by a pressure change in the surrounding container generated by an activatable gas generator that generates pressure within the first region that causes the liquid to be expelled. The patent application describes two types of medication units—Type A and Type B—and types device construction to operate said medication units types. The Type B configuration comprises a medicament reservoir having flexible walls possibly Made from films or foils. The medicament is pressurized by exposing the reservoir wall to external pressure. Upon pressurizing the medicament a portion of the wall is displaced toward a rupturing member, thereupon the reservoir is ruptured and the medicament is expelled toward the administration means. U.S. Pat. No. 6,258,063 further describes means for controlling the pressure applied to the reservoir. Since this patent is limited pressurizing means which instantly deliver high pressure to the reservoir, provided by explosion, it does not refer to control mechanism that which prevent the rupture if the pressure in the reservoir has not reached a defined threshold. On the contrary, U.S. Pat. No. 6,258,063 refers to situation where it is needed to get rid of excess pressure due to the excessively high pressure that the explosion can generate. Thus the pressure control in U.S. Pat. No. 6,258,063 is limited to control of exhaust of the combustion products.

U.S. Pat. No. 6,258,063 also describes means of sealing the ruptured area around a fluid conduit such that the medicament is directed to the fluid conduit leading to the administration device. The sealing is achieved by venting the area around the ruptured portion which causes the walls around the ruptured area to press against the walls around the fluid conduit due to the high pressure of the medicament, forming a surface to surface seal between the wall of the reservoir and the wall around the rupturing member.

The apparatus related to as Type B in U.S. Pat. No. 6,258, 063 seem very similar to the present invention but has some technical drawbacks which are overcome by the present invention. In U.S. Pat. No. 6,258,063 the reservoir is ruptured by the rupturing member prior to establishing the sealing of the reservoir wall around the rupturing member. It is supposed that the inventors have assumed a very reliable sealing between the rupturing member and the reservoir wall prior to establishing the sealing between the reservoir wall and the walls around the rupturing member otherwise some of the medicament is due to leak out in the transition time. But this assumption in unlikely to hold when the sealing is to happen between a very thin needle and a thin wall in particular with a Polypropylene wall which is relatively rigid material. Disadvantageously, such leakage would not only affect the accuracy of the administered dose but would also expel the leaked medicament to the surrounding, potentially exposing other people to the medicament. It is also likely that the inventors of U.S. Pat. No. 6,258,063 has assumed that the transition time between the rupturing of the reservoir wall, and the time that said wall form a tight seal with the wall around the rupturing member to be very short and so in the worst case an insignificant amount of medicament will be expelled. While this assumption may be acceptable for certain indications it may be poor for others where highly accurate dose is required or where expelling the leaked drug to the environment is not acceptable. Therefore, while the present invention adopts the rupturing configuration of the Type B apparatus of U.S. Pat. No. 6,258,063 for certain embodiments, it also proposes alternative advantageous embodiments with improved rupturing mechanism which prevent any leakage of deliverable fluid, which is essential where accurate dose administration is obligated.

A further technical limitation of the apparatus related to as Type B in U.S. Pat. No. 6,258,063 is that the medication unit which consist of two major walls is being sandwiched between a first shell and a second shell. While this construction is feasible and acceptable for some embodiments it has several disadvantages: 1) it unnecessarily complicates the manufacturing assembly as the reservoir participates in the construction of the handling device, 2) it introduce unnecessarily sealing failure modes as the reservoir wall participate in the sealing of the handling device, 3) it introduce super demands from the reservoir wall which has to comply with several functions, and 4) Fixing the reservoir walls to the handling unit can introduce excessive stresses in the wall vs. otherwise pure pressure, and 5) more constrains between components in an assembly means tougher tolerance challenges. While said construction has been adopted by the present invention for certain embodiments of the present invention, the present invention presents an advantageous construction where the reservoir is an independent unit accommodated with in the handling device and not participating in the construction of the handling unit, thus overcoming the above disadvantages. The present invention thus presents several advantages including simplifying the manufacturing assembly, reduce sealing failure modes, and reduce unwanted stress from the reservoir walls.

Also, the apparatus described in U.S. Pat. No. 6,258,063 is limited to a specific form of application where a single medicament is instantly delivered to the skin, and does not comply with any application where more than a single substance has to be stored and delivered.

Drug administration means which incorporate means for mixing or constituting drug components are known in the art. U.S. Pat. No. 7,011,650 describes multi-dose syringe, and US patent application 20040249339 describes an injection device that to inject sequentially two fluids into a patient. Both of these patents describe complex constructions utilizing a piston and a barrel which will be expensive to manufacture. The reservoirs in these patents comprise rigid wall portion and rubber sealing members which are mostly unsuitable for long term storage of pharmaceutical compounds from the time of manufacturing to the time of administration.

Also, the present invention proposes means for lowering the pressure requirements for penetrating the skin there for lowering the pressure withstand demand from the apparatus.

All of the above needle-free injectors are hand held devices for administration by a care giver or self-administration. For various reasons it is advantageous to have a needle free device in a fashion of a patch. One reason is the fear factor. One of the advantages of needless injectors over regular syringes is the increased compliance due to the avoidance of needles which cause resistance by many patients. Yet, needleless injection is painful and so fear resistance may still exist by many patients which my cause the patient to move during administration. Such movement can affect the efficiency of the administered dose penetration, and in the worse case can injure the patient. The jet of a needless injector is capable of cutting the skin if it points in the wrong angle to the skin. It is therefore advantageous to device the procedure to two stages into a) attaching a patch device to the skin, b) activate the device, c) injection is performed after a short delay, and d) remove the patch. For self administration it will be an easier procedure to first locate the device on the target place on the body and then activate the device, rather than doing the two functions at the same time. It is therefore the object of the invention to provide a patch fashion needleless injector.

Hypodermic drug delivery devices which comprise internal deliverable fluid reservoir, an administration needle, and insertion mechanism for inserting the needle are well known in the art. Particularly interesting are those devices in which said administration needle is disconnected from said reservoir until the time of activation at which point the devices manipulates the reservoir and the administration device to establish fluid communication. Despite the fact that the drug reservoir in said devices is confined in the device it is completely sealed and merely provide a packaging means, eliminating exposure and therefore influence of further elements in the device on the deliverable fluid, as well as reducing leakage risks. U.S. Pat. No. 6,979,316 presents an auto-injector for rapid delivery of a bolus. The patent teaches a mechanism for extending an administration needle from a first concealed position in the package to an exposed position, followed by rupturing of said reservoir by a rupturing member which establishes a fluid communication between the reservoir and said administration device. At a subsequent step the reservoir is pressurized by yet another part of said mechanism. The differentiation of parts of the mechanism to different functions of U.S. Pat. No. 6,979,316 result in a relatively complex mechanism. Also the fact that the reservoir is first ruptured followed by pressurizing the reservoir puts higher demands on the pressurizing mechanism to react fast in order to release a bolus from said reservoir. U.S. Pat. No. 5,957,895 presents yet another idea of a drug delivery device comprising a hypodermic needle and a reservoir which are disconnected until the time of activation. The pressurizing mechanism of the reservoir in the above prior art comprise separate mechanisms or sub-mechanisms for creating fluid communication between the reservoir and the administration device, and for propelling the deliverable fluid, resulting in redundancy of mechanisms which effect complexity and costs of these apparatuses. The present invention comprises a pressurizing device for propelling the deliverable fluid from the reservoir to the body of a patient, where said pressurizing device is also responsible to urge the reservoir rupture and the needle insertion therefore simplifying the apparatus and reducing manufacturing costs. It also establish an inherently logical sequence in which the deliverable fluid can not be expelled prior to the insertion of the administration device to the body of the patient.

An apparatus which apparently has many similarities with the apparatus of the present invention is featured in U.S. Pat. No. 6,656,147 (here after referred to as U.S. Pat. No. 147). U.S. Pat. No. 147 describes a device for delivering a substance into the skin of a patient includes a housing and a plurality of microneedles for penetrating the skin. The housing includes a bottom wall with a plurality of apertures for supplying the substance to the microneedles. The housing also includes a flexible top cover member enclosing a bladder containing the substance to be delivered. The bottom wall of the housing has at least one cannula facing the bladder. Pressing on the top cover member causes the cannula to puncture the bladder and deliver the substance to the microneedles for delivery to the patient. In one embodiment, the cannula is surrounded by a flexible member to prevent piercing of the bladder until sufficient pressure is applied to the cover member to depress the flexible member. Therefore U.S. Pat. No. 147 provides a pressurizing device which pressurizes a reservoir, in a form of a pre-sealed bladder, forcing the bladder against a rupturing member to rupture the bladder and to establish fluid communication between the reservoir and the administration device. Unlike the present invention U.S. Pat. No. 147 does not teach that the reservoir and the area around the rupturing member should establish a fluid tight seal, in fact U.S. Pat. No. 147 suggests the opposite where the area between the reservoir and the rupturing members is part of the fluid passage from the reservoir to the administration device. This raises a list of concerns that are not particularly addressed by U.S. Pat. No. 147 and are listed here under:

a) contamination—the space between the bladder and the base (where the rupturing members are located) is exposed to contamination from the time that the apparatus has been removed from the package to the time that the cover is closed.

b) The chamber in which the reservoir is accommodated contains air (by definition of the description in this patent) which will be exposed to the deliverable fluid after rupturing of the reservoir and most likely be delivered to the body of a patient. While it might not be desirable to administrate air to begin with, in this case the air is ambient air that was picked up prior to closing the cover, therefore bare a contamination risk, as well as unpredictable dose size. In fact if the cover establish an air tight seal with the chamber where the reservoir is accommodated (U.S. Pat. No. 147 is not clear about this point) than it is most likely that air will be delivered to the patient when the chamber is pressurized, even before the reservoir has been ruptured.

c) If the cover does not establish a fluid tight seal with the chamber then the deliverable fluid can be spilled from the apparatus and effect the dose accuracy. It is also unclear in this case what propels the deliverable fluid to the administration device as (if the cover does not establish a fluid tight seal with the chamber) the chamber is not pressurized.

The apparatus of the present invention overcomes the above disadvantages by providing a fluid tight seal between the reservoir and the area around the rupturing member.

It is unclear from U.S. Pat. No. 147 whether the cover establishes a fluid tight seal on the chamber where the reservoir is accommodated. The invention summary, as well as the descriptions and the claims do not refer to pressurizing the chamber but just to pressurizing the reservoir and therefore we argue that the apparatus of U.S. Pat. No. 147 is not practical for the purpose of administrating fluids to the body.

Unlike the present invention, U.S. Pat. No. 147 does not provide an auto-insertion mean or auto retraction means of the administration means which present a contamination and injuries risk.

U.S. Pat. No. 147 teaches a method for drug reconstitution by having a first ingredient in the reservoir and a second ingredient, in a dry form, in the fluid passage from the reservoir to the fluid exit of the administration device. Disadvantageously this second ingredient is exposed to ambient air until the cover of the apparatus has been closed. Another disadvantage is that there is no time for the ingredients to interact prior to administrating to the body. The present invention overcomes these disadvantages by storing the ingredients in sealed and separated compartments in the reservoir. The present invention provides the time necessary for the ingredients to interact prior to administration.

U.S. Pat. No. 6,780,171 (here after referred to as U.S. Pat. No. 171) features a further apparatus, generally from the authors of U.S. Pat. No. 147, that overcomes part of the disadvantages of the last by featuring a fluid tight seal communication between the reservoir and the area around the rupturing member (in the embodiment presented in U.S. Pat. No. 171 we refer to the rupturing member as the tip of a needle, and the area around the rupturing member is the inlet to the conduit from the reservoir). The invention of U.S. Pat. No. 171 does not provide means for conditioning a threshold pressure prior to rupturing the reservoir and it does not seem the intension of this invention to have a threshold pressure prior to rupturing. While this may not present a disadvantage with the administration means suggested by U.S. Pat. No. 171, it does present a disadvantage with other administration devices covered by the present invention including a needleless injector. The apparatus of the present invention provides a rupturing-control mechanism which conditions the rupture with the presence of a threshold pressure in the reservoir. U.S. Pat. No. 171 does not provide means for preventing rupture of the reservoir prior to having the administration device properly communicating with the body of the patient, and therefore accidental or premature closing of the cover will result in rupturing of the reservoir and spillage of the deliverable fluid. The apparatus of the present invention overcomes this disadvantage by providing a safety catch which prevents activation if the administration device is not properly communicating with the body of the patient.

Lastly the reservoir of U.S. Pat. No. 171 comprises a complex assembly which includes the rupturing means and the administration means and is not very convenient and safe to run in automatic filling processes, and in particularly not in standard or retrofitted filling lines such as form-fill-seal manufacturing lines. The present invention overcomes this disadvantage by providing a simple reservoir construction which is well adequate for processing and filling by standard equipment in the industry.

It is therefore the object of this invention to provide a pressurized hypodermic drug delivery apparatus where the drug can be delivered directly from a none-expensive sterile storage package.

It is a further object of the invention to provide an apparatus for administrating combination drugs.

It is a further object of the invention to provide an apparatus for reconstitution (resuscitation) drugs.

It is a further object of this invention to provide an apparatus for instantly delivering pressurized drug using a relatively slow pressure building device therefore allowing simpler and less expensive pressure building mechanisms to be utilized.

It is a further objective of the invention to reduce the parts count and in particular the moving parts and sealing members.

It is a further object of the invention to provide a simple and inexpensive safety catch.

It is a further object of the present invention to provide a hypodermic drug delivery apparatus which requires relative low pressure for penetrating the skin.

It is a further object of the invention to provide an electronic circuitry for monitoring and controlling the apparatus function.

It is further the object of the present invention to provide means for monitoring the drug conditions and history.

It is a further object of the invention to provide means for conditioning the drug prior to administration.

It is a further object of the invention to provide a reservoir that complies with the objectives of the apparatus of the present invention.

It is a further object of the invention to provide an electronic circuitry for monitoring and controlling the apparatus and the administration which is at least partially comprised in the reservoir assembly.

It is a further object of the invention to provide a needleless hypodermic injection apparatus in a patch fashion.

Those and other objectives of the invention will become clear in the description of the invention.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

SUMMARY OF THE INVENTION

Therefore it is the objective of the present invention to provide a hypodermic drug delivery apparatus for delivering a pressurized medication fluid that over comes the disadvantages presented in the prior art. The apparatus of the present invention comprises a reservoir containing at least one deliverable fluid, and a rupturing member, said reservoir having at least one portion of at least one wall rupturable by said rupturing member. The apparatus also comprises a pressurizing device, a fluid conduit and an administration device, and the arrangement is being such that upon rupturing said reservoir said deliverable fluid is expelled via said fluid conduit to the administration device and into the target tissue, due to pressure generated by the pressurizing device. The pressurizing device pressurizes the fluid in the reservoir by applying force or pressure to at least one displaceable wall of the reservoir. In the apparatus of the present invention a rupture-control mechanism which prevent the rupture of the reservoir under a defined pressure threshold. The rupture control mechanism provides opportunity for several amendments over the prior art (in particular U.S. Pat. No. 6,258,063) that will be emphasized in the description of the embodiments provided here under: a) the rupture control mechanism enable a secure sealing between the fluid conduit and the reservoir wall prior to rupturing the reservoir, b) it provides a safety feature which prevents accidental activation of the device, c) the rupture-control mechanism provides a compliance feature which prevents administration of the deliverable fluid under inappropriate conditions, and d) it opens possibility to use alternative pressurizing means to the fast rising pressurizing mechanisms to which the prior art is limited.

In a preferred embodiment of the apparatus of the present invention the reservoir is a pouch made from a single or multi-layer films or foils. Foils and films have excellent barrier properties and are approved for storing pharmaceutical substances. At the same time films and foils are suitable for easily rupture with a sharp object especially when they are under strain. Films and Foils are very inexpensive medias as well as the manufacturing process for making packages from these medias. Means for forming, filling and sealing packages made from thin plastics are widely discussed I U.S. Pat. No. 6,258,063. Thus pouch is an excellent media to both store the drug and to serve as the drug reservoir of the apparatus of the present invention, providing an advantage on prior art where piston/cylinder arrangement are provided for the reservoir construction. In a further preferred embodiment the wall comprises a resilient layer or portion which enhances the sealing of the reservoir wail against the fluid conduit. Said resilient portion can be maintained in a compresses state to further enhance the sealing around the rupturing member. A particular case of a compressed resilient sealing member is a septum commonly used in the medical field for connecting between fluid transporting devices. In some embodiment the rupturing arrangement is such that the area around the portion of the reservoir that is to be ruptured, and the area around the rupturing member are engaged to a fluid seal contact before the rupturing occurs, as opposed to the design demonstrated by U.S. Pat. No. 6,258,063 Type B.

The films and foils that constitute at least portion of the walls of the reservoir of the present invention can be joined by heating and melting or partly melting the layer that is to be sealed. Alternatively said foils or films can be joined by other means including gluing, by permanently pressing the edges together, by stitches, etc. The strength of the joint can be controlled by various parameters such as the active joint surface properties, the materials that have been bonded, and the parameters of the joining process such as heat, time, and pressure applied to the bonding area. It is therefore common and convenient to create weakened areas in the joining areas of the walls that can be separated. In some embodiments of the present invention the reservoir comprised more than one compartment. In one embodiment at least two compartments are merged by separating the joint which partitioned between said compartments, and their content are mixed, thereafter the mixed fluid is delivered according to the method of the present invention described above. The merging of separate compartments is advantageous for combination drug therapy and for reconstitution (resuscitation) of pharmaceutical substance. Combination drug therapy refers to procedures where more than one pharmaceutical ingredient has to be delivered but said ingredients can not beheld together for a significant time, for example because of chemical or biological stability reasons or regulatory reasons. In some embodiments one compartment includes a liquid substance such as saline and the other a drug or vaccine in a dry form. Dry forms of drag include lyophilized, loose powder, compressed powder, or solid. In many cases it will be advantageous to keep the active materials in a dry form and mix them with their liquid part just before use. In the case of vaccines such combination is referred to as reconstitution or resuscitation. In some embodiments the deliverable contents of the separate compartment s of the reservoir are delivered simultaneously or in a sequence without pre-mixing.

In one embodiment of the apparatus of the present invention, the deliverable fluid from the reservoir mixes with at least one additional ingredient after it has been expelled from the reservoir.

In a further preferred embodiment the reservoir comprises at least one filling port to fill an ingredient to at least one compartment. The filling from the filling port can be in the filling line or just prior to administration or at any stage in between. The filling through the filling port can be to an empty compartment, to a partly prefilled compartment or to a fully filled case, the last will cause the compartment to merge with a second compartment as described above.

The rupturable portion of the wall can be elastic and is stretches under the presence of pressure in the reservoir causing a displacement of at least part of the rupturable wall portion. This property is utilized in various embodiments for the rupture-control mechanism. In one embodiment said displacement is utilized to bring said wall portion in contact with the rupturing member and cause the rupturing of the wall. In a further embodiment the displacement of said portion of the wall is utilized to advance said portion of the wall to a position where it can be reached by the rupturing member. The advancement of the rupturing member to rupture the wall is conditioned by other events. In this embodiment the stretching of the wall portion does not directly activate the rupturing but instead provides an "arming" feature of the apparatus which can now be ruptured by a further rupturing action in which the rupturing member in brought in contact with the rupturable wall portion.

In other embodiment the rupture-control mechanism does not utilize the stretching of the wall for activating or arming the apparatus, and thus the reservoir wall in these embodiments is not necessarily stretchable. In some embodiments the reservoir is accommodated on a moving plate which is urged away from the rupturing member by a biasing spring such that the rupturing member can not reach the reservoir wall. Then, under the presence of pressure in the reservoir the moving plate is forced to displace to a position where rupturing can occur. Other rupture-control mechanisms will become evident in the embodiments described here after to emphasis the extent of the rupture-control mechanism. Other mechanisms can provide safety catch that prevent rupturing under certain conditions, including mechanisms that prevent the use of the apparatus prior to presence of pressure or prior to firmly pressing the apparatus against a target surface, or preventing accidental (none-voluntary) use of the apparatus.

In some embodiments a resistance-mechanism is incorporated that prevent the reservoir from pressurizing until a threshold pressure or force is delivered by the pressurizing device, upon which the resistance-mechanism allows the pressurizing-device to pressurize the reservoir. The reservoir is then pressurized instantly even if the pressurizing device has a slow pressurizing nature. Examples of pressurizing devices with slow pressurizing nature include: a) a relatively low capacity compressible fluid pump, b) a spring loaded rod which requires repeated or long action to get loaded, c) a gas generating chemical reaction.

In some embodiments a safety catch is incorporated to prevent accidental use or non-complying usage of the apparatus.

Other mechanisms can be incorporated to give indications to a person about the state of the apparatus. A visual indication means of the progress of the drug administration by providing a window in the device through which the spring that pushes on the reservoir is visible is provided by U.S. Pat. No. 6,780,171 incorporated here by reference. Another visible indication means for indicating the delivery of a sufficient amount of the substance to the patient is provided by U.S. Pat. No. 7,115,108 incorporated here by reference. The indicating means is visible from the exterior of the delivery device. In some embodiments, the indicating device is an elastic expandable diaphragm which, when the cavity is filled with a substance, creates the dispensing pressure.

The pressurizing device can be any device that can provide the necessary pressure for proper performance of the apparatus. While all the pressurizing mechanisms stressed in the prior art are applicable for the apparatus of the present invention, the apparatus of the present invention can advantageously utilize other pressurizing devices as well which have a slow pressure building nature. In the prior art devices the pressure in the pressurizing means e.g. a pressure chamber is directly effecting the pressure of the deliverable fluid. Therefore where a large pressure step-up is required to penetrate the skin, the pressurizing device will have to provide such a pressure curve, i.e. a fast pressure generating pressurizing-device is required. This requirement complicates the pressurizing devices or alternatively limits them to a few relatively simple pressurizing devices. The device of the present invention incorporate a rupture-control mechanism which prevents the delivery of the deliverable fluid before a defined pressure has been built in the reservoir. That said, slow pressure building devices are compatible for the present invention including the examples stressed here: In one embodiment the pressurizing device comprise a spring and a spring loading mechanism said loading mechanism can be loaded (or drawn) by performing several repeated actions stressed over time, none of which will enable rupturing until the required threshold pressure in the reservoir is obtained. In a further embodiment the reservoir is confined in a pressure chamber and the pressure chamber is pressurized by an external foot pump connected to the pressure chamber with a hose. In a yet further embodiment of the present invention the pressure chamber is pressurized by a chemical reaction internal to the pressure chamber. This chemical reaction can slowly build pressure. An example of such a reaction is the reaction between citric acid (aqueous) and soda powder which generate carbon dioxide. The reagents can be stored in the pressure chamber (and introduced by external manipulation of the apparatus), or introduced to the chamber during the preparation process of the apparatus. In one embodiment the compartments that store the reagents are part of the pouch assembly.

In some embodiments the pressure release mechanism is incorporated to get rid of excess pressure generated by the pressurizing device. Examples of pressure control arrangements which release excess pressure are described in U.S. Pat. No. 6,258,063, incorporated here by reference.

Some embodiments of the drug delivery apparatus of the present invention further comprise anti-abuse mechanism which prevents extraction of fluids from the reservoir after the completion of the treatment. In one embodiment the anti-abuse mechanism disconnects the fluid communication between the fluid conduit and the reservoir. In another embodiment the anti-abuse mechanism prevents access to the administration device. In some embodiments the anti-abuse mechanism prevents access to the administration device after the completion of the administration procedure.

Alternative administration means can be incorporated with the apparatus of the present invention including a needless injection orifice or orifices, a hypodermic needle or needles, a micro-needle or micro-needles array, or a tube or conduit leading to a target tissue or organ, or leading to a further administration device.

The entire prior art needleless injectors are handheld devices. For several embodiments of the apparatus of the present invention, where a slow pressurizing device is incorporated, it is preferred to attach the apparatus to the skin in a patch fashion. With that approach the apparatus can be attached to the skin of the patient and be removes after a given time (say 5 minutes) or upon an indication that indicate the administration has completed. In some circumstances a patch form needless injector will increase user compliance. Despite the avoidance of the needle, needless injection are painful and it is very possibly that a patient fear element will be associated with the procedure effecting the compliance of the apparatus—in one scenario a patient may have resistance to accepting the procedure, and in another scenario the patient may be performing undesirable move due to fear at the instant of the administration. It is possible that when a needles injector is not held firmly and appropriately against the skin the administration results in injury as the jet cuts the skin tissues. The patch configuration avoids such injury risk. A patch apparatus will increase compliance in self administration procedures both because of the fear element described above and because it is easier to handle the procedure if positioning and activation are not to be performed simultaneously.

The apparatus of the present invention can take form of a disposable, semi-disposable or multi-use product. While it will make sense in many applications to dispose the reservoir after a single administration, the reservoir can take form of a refill set that can be used for several administrations limited only by the times that the rupturable portion of the wall can reseal. In some embodiments only portions of the apparatus are intended for multi-use such as the pressure reservoir. In some embodiments the entire apparatus is confined in a sterile package, in other embodiments only a portion of the device is maintained in a sterile package. For example in one embodiment the assembly of the reservoir, the rupturing means, the fluid conduit and the administration means are kept in a sterile package. In some embodiments at least a portion of at least one of the walls of the reservoir provides a portion of the sterile package.

In some embodiments the apparatus of the present invention comprises at least part of an electric or electronic circuitry. The electronic circuitry may comprise several components including a power source, IC, sensors and transducers human interfacing means (light sources, buzzers, LCD or 7-seg display . . . ), machine interfacing means (transmission circuits . . . ), recharge circuitry (photovoltaic, vibration, etc.) and part or all of the pressurizing means (such as a pump, actuator, transducers, encoders, and sensors), etc.

The circuitry may serve for several functions examples to which include:

a) monitor the apparatus or reservoir history parameters such as temperature, humidity, acceleration (g), pressure, time from opening, time from manufacturing, time from filling, exposure to light, battery condition (if such is incorporated).

b) Monitor properties of the administration procedure such as pressure, temperature, displacement of the reservoir wall and volume of the reservoir or the pressure chamber.

c) Analyze the monitored parameter and conclude on the status of the apparatus, the reservoir, or the deliverable fluid, and its validity.

d) Communicate information to a person or another device, such as information on the status of the device, expiration of the device, validity of the device, time to administrate, successfulness of the administration procedure.

e) Provide at least part of the pressurizing device.

f) Provide control of the pressurizing device, in particular close loop control.

g) Prevent unauthorized or none-complying use of the apparatus.

h) Condition the deliverable fluid for delivery, for example heat or cool the fluid to a desired temperature, stir the fluid using a stirrer, or ionize/galvanize the fluid via electrodes where this is desired.

i) Provide at least part of the safety catch mechanism.

In some embodiments at least part of said circuitry is integrated in the pressure chamber. In further embodiments at least part of said circuitry is integrated in the reservoir assembly, either internal to the reservoir, external to the reservoir, confined in the reservoir wall or a combination of the above. Integrated electronic assemblies is film layers of the like are described in U.S. Pat. No. 6,924,164 incorporated here by reference.

It is another object of the invention to provide a multi-compartment reservoir for hypodermic drug delivery apparatuses. It is a particular object of the invention that said reservoir will provide a sterile package for at least one of the deliverable ingredients. It is yet another particular object of the invention that the reservoir will be an independent assembly from the delivery apparatus. That means that the reservoir is accommodated in the apparatus but it is not providing a function in the apparatus construction (such as seal or a joint, or a guide or a stopper, etc.) between the elements of the apparatus. Depending on the design of the reservoir and the apparatus the reservoir can be operated to deliver the different ingredients simultaneously or in a sequence.

In some embodiment at least two compartments are merged to mix the ingredients there in prior to administration to the patient body. In some embodiment the compartments are separated by a sealed joint which is separable under an adequate force applied to the joint. In some embodiment said force is a result of pressurizing at least one of the compartments. In some embodiments said pressure is a result of manually depressing said compartment. In other embodiments said pressure is applied be a pressurizing device of the apparatus. In yet other embodiments said pressure is applies be another instrument. In some embodiment there is a time lag between merging compartments and the delivery in order to let the ingredients from the compartments mix and/or react. In some embodiments the apparatus receiving said reservoir comprise at least part of a mixing device to facilitate the mixing of the ingredients of the compartments that have been merged. In other embodiment said reservoir comprise at least part of a mixing device to facilitate the mixing of the ingredients of the compartments that have been merged.

In some embodiments of the multi-compartment reservoir there is more than one separable joint which seal between two adjacent compartments. In some embodiments said separable joints require distinguished separating force or pressure to be separated. In some embodiments the apparatus receiving said reservoir comprise a pressurizing-device which gradually increases the pressure in at least one compartment of the reservoir causing said joints to separate in a timely sequence in accordance with said pressurizing process. In some embodiments the pressure required to separate said joint is smaller than the pressure required for rupturing the reservoir therefore the compartments will merge and the ingredients of these compartments will mix forming a new deliverable fluid, before delivering said deliverable fluid to the patient. In other embodiment the pressure required to separate the joint between a first compartment and a second compartment is higher than the pressure required for rupturing said first compartment therefore the deliverable fluid of the first compartment will be delivered to the body first following the delivery of the deliverable fluid of the second compartment after the joint between said first compartment and said second compartment has been separated.

Some embodiments of the multi-compartment reservoir comprise at least part of the electronic or electric circuitry described above.

In one embodiment of the multi compartment reservoir at least one compartment contain at least one ingredient associated with the pressurizing mechanism which upon breaching the capsule and exposing said ingredient to either the volume of the pressure chamber or the volume of a second capsule, said ingredient will participate in a pressure generating chemical or physical process.

In some embodiments of said multi-compartment reservoir at least one compartment comprises a filling port. In some embodiments said compartment's content is an ingredient or ingredients to be delivered to the body during the administration. In other embodiments the content of said compartment is a reagent or otherwise an ingredient associated with the pressurizing device. In some embodiments at least one filling port serves to fill the compartment in the manufacturing-filling line. In other embodiments at least one filling port serves to fill a compartment in the preparation prior to the administration procedure. In one embodiment said filling port serves to fill an empty compartment. In a further embodiment said filling port serves to fill a semi-filled compartment. In yet another embodiment the filling port serves to fill a full compartment, is which case one of the following will occur: a) at least one of the walls will stretch causing the compartment to pressurize, b) a seam of the compartment's walls will breach and extend the compartments volume yet keeping the content of the compartment isolated, c) a seam of the compartment's wall will breach into a second volume containing a distinguished ingredient or ingredients.

One example is a compartment which is associated with the pressurizing mechanism which is empty during storage. The compartment comprises a filling port for filling citric acid solution prior to the administration procedure. The compartment is urged to be filled beyond its original volume causing a weakly joint to separate breaching said compartment into a second compartment which contains sodium bicarbonate powder. The ingredients of the two compartments will mix and initiate a gas generating reaction; the pressure of said reaction is used for the pressurizing device to pressurize at least one deliverable fluid compartment. In a further embodiment the sodium-bi carbonate powder is micro-encapsulated to controllably delay the exposure to the acidic solution and the gas generating rate. In a further embodiment a different chemical reagents are used.

It is a further object of the invention to provide a needleless hypodermic injector in a form of a patch, such that the apparatus is attached to the body of the patient during the delivery of the deliverable fluid with out having a person (the patient or a caregiver) having to hold the apparatus in this position. In some embodiments the apparatus is attached to the body of the patient prior to activating the pressurizing device. In other embodiments the apparatus is attached to the skin after the pressurizing device has been activated. In some embodiments there is a time delay between the activation and the actual delivery of the deliverable fluid due to the slow pressure buildup of the pressurizing device. In other embodiments a time delay is implemented between the time of activation and the time of the actual delivery, to let the content of at least two compartments mix. In other embodiments a time delay is implemented between the time of activation and the time of the actual delivery, to allow reconstitution (resuscitation) of the deliverable formulation. The patch apparatus is attached to the body of the patient by one of the means known in the art including: an adhesive pad, straps, or adhesive bands.

BRIEF DESCRIPTION OF THE DRAWINGS

FIG. 1 presents general views and exploded view of a preferred needleless patch embodiment of the drug delivery apparatus of the present invention.

FIG. 4 presents various section views and detail views of another preferred embodiment of the drug delivery apparatus of the present invention where the administration device is a hypodermic needle.

FIG. 7 presents a further preferred embodiment where the pouch comprises two separate compartments of deliverable substances.

FIG. 12 present a further preferred embodiment of the present invention where the reservoir provides a portion of the sterile package.

FIG. 13 demonstrates a further preferred embodiment of the device of the present invention comprising a hypodermic needle administration device.

FIGS. 15-17 illustrate manners in which the reservoir's compartments can be manually mixed.

DETAILED DESCRIPTION OF THE INVENTION

Figure 2A:
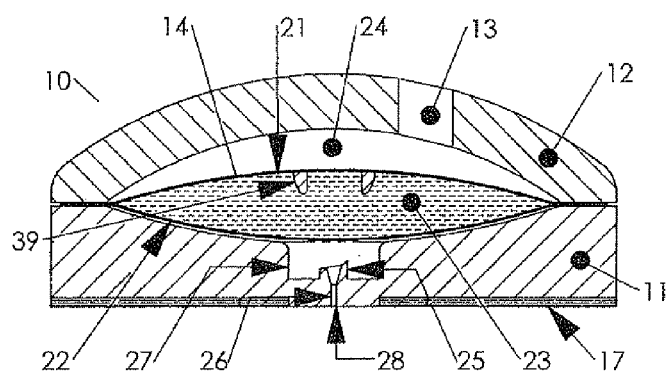
FIG. 2 presents section views of the preferred embodiment of FIG. 1 at various operation positions.

Referring to FIG. 1a, a perspective view of a preferred embodiment of the present invention is demonstrated showing the external elements of a needleless hypodermic injection apparatus in a patch form 10. The apparatus 10 comprises a base 11 and a cover 12, and an adhesive layer 17 for attaching the apparatus to the skin of a patient. The adhesive layer 17 is covered with a removable protective layer 18 which is removed prior to attaching the apparatus to the skin. Alternatively, the apparatus can be attached to the skin by other means known in the art including: a) adhesive tapes that will be placed over the apparatus and attach to the skin, b) glue, c) straps, or d) by actively holding the apparatus firmly in place e.g. with the hand. The apparatus further comprises a pressurizing device for pressurizing the deliverable fluid or fluids in the reservoir. In this embodiment the pressurizing device comprises and external pressure source which supplies a pressurized fluid (in a gas, or liquid form) via port 13 to a pressure chamber (will be demonstrated in subsequent figures). FIG. 1b demonstrates an exploded view of the apparatus, exposing a reservoir 14 located between the base 11 and the cover 12, said reservoir contains at least one deliverable pharmaceutical grade substance. At least a portion of the walls of said reservoir are made from film or foils (referred here after as films). Where the reservoir 14 is mostly made from films, as is demonstrated in FIG. 1b, the reservoir can be referred to as pouch.

The reservoir walls are sealed together to form a sealed sterile package for the pharmaceutical content.

Referring now to FIG. 1c, a slightly different version of the embodiment of FIGS. 1a and 1b is demonstrated where the pressure port 13 is eliminated. In this embodiment the pressurizing device does not require an external pressure supply, as will be detailed in the following text. Any of the pressurizing devices described in the prior art are applicable for apparatus of the present invention. On top of that, the present invention introduces some novel pressurizing-devices which will be described here after.

Referring now to FIG. 2a, a section view of the embodiment of FIG. 1a is demonstrated in the rest position of the apparatus 10 (i.e. prior to activation). The pouch 14 consists of a $1^{st}$ wall 22 and a second wall 21 which are sealed along their peripheral edges defining a sealed sterile volume for the deliverable fluid 23. Preferred sealing method is heat sealing which melts or partly melts the joint surface of the film to form a joint with reciprocal wall. Examples of heat joint methods include: heat stake, ultrasonic, vibration, RF, IR, or other means known in the art. Alternative joint methods include, glue, adhesive layer, stitching, or pressing the joint walls together via further mechanical arrangement. Joint methods are listed and described in U.S. Pat. No. 6,258,063 incorporated here by reference. U.S. Pat. No. 6,258,063 further describes pre-filling methods of flexible reservoirs, incorporated here by reference. In one embodiment the reservoir comprises at least one filling port for filling or partly filling at least one compartment of the reservoir.

In the present embodiment the peripheral edges of the pouch 14 are tightly held between the base 11 and the cover 12, such that a fluid tight sealed pressureable cell (i.e. "pressure chamber" 24) is formed between the cover 12 and the pouch 14.

The base 11 accommodates the $1^{st}$ wall 22 of the pouch 14 and has a recessed section 27 in which a rupturing member 25 is located. A fluid conduit 26 leads from the recess 27 to the administration means 28 which in this embodiment is in the form of a needless injector orifice.

In the rest position demonstrated in FIG. 2a, the reservoir 14 is not pressurized and the $1^{st}$ wall 22 of the reservoir 14 is offset from the rupturing member such that a rupture of the reservoir can not occur.

Figure 2D:
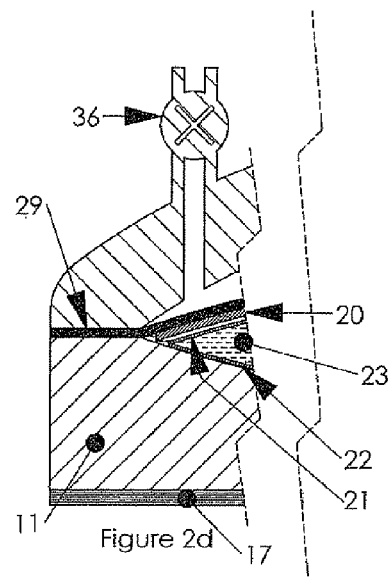
Figure 2B:
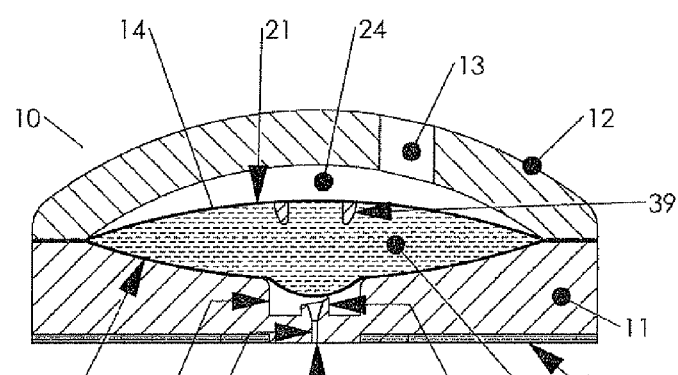

FIG. 2b demonstrates an intermediate state of the pressurizing process of the apparatus 10. In this position the pressure chamber 24 is partially pressurized which in return pressurize the deliverable fluid 23, by pressing the $2^{nd}$ wall 21, thereby causing the $1^{st}$ wall 22 of the pouch 14 to stretch out into the recess 27 and get to proximity with the rupturing member 25. FIG. 2c demonstrates the next step in the pressurizing process, where upon additional stretching of the $1^{st}$ wall 22, it comes in contact with the rupturing member 25 causing the wall 22 to rapture and the deliverable fluid to burst into the flow conduit 26 and through outlet orifice 28 into the patient's skin. The above described mechanism prevents the rupture (and therefore administration) with the presence of a pre-defined threshold pressure in the reservoir and is here after referred to as "rupture-control mechanism". The fluid delivery will continue until the pouch empties out or until the pressure in the pressure cell drops or is being removed. The stopper 39 is implemented in the pouch to avoid damage of the rupturing member 25 to the second wall 21 as said $2^{nd}$ wall 21 is reaching the $1^{st}$ wall 22, upon emptying the reservoir 14. The stopper 39 can be made of any material compatible with the deliverable fluid 23 and with other regulatory requirements, including certain molded or extruded polymers, stainless steel, porous substance such as Porax™. The stopper 39 can be implemented on the $1^{st}$ wall 22 or the $2^{nd}$ wall 21. It can be attached to the wall by means of welding or gluing or other attachment means known in the art, or it can be implemented between the layers of a film wall. The stopper may comprise grooves, holes, or porouses creating a fluid communication passage between its outer diameter surface and the inner diameter surface such that when the reservoir is about to empty and both the $1^{st}$ and the $2^{nd}$ walls 22-21 are in contact with the stopper, remaining deliverable fluid 23 from the peripheral of the reservoir can reach the fluid conduit 26. It will be obvious to those skilled in the art that other means known in the art can be implemented to prevent the rupture of the second wall. For example the central section of the $2^{nd}$ wall 21 can have a construction that is damage proof by the rupturing member 25. Therefore stopper 39 will not appear in several of the following embodiments, but it should not be deduced that this concern has been neglected. In some embodiments stopper 39 also assist in keeping fluid communication between the deliverable fluid 23 in the peripheral zone of the reservoir 14 and the ruptured section, preventing risk of potential shutoff between walls 21 and 22. The stopper 39 can be made from resilient material such that it could be squeezed into residual volume of the reservoir 14 as the residuals of the deliverable fluid 23 are depleting.

In one embodiment the rupture-control mechanism comprises a resilient member which is accommodated in recess 27 and protecting the rupturing member 25 such that the first wall 22 of the reservoir 14 has to push on said resilient member in order for the rupturing member 25 to be exposed and rupture the $1^{st}$ wall 22. Said resilient member can be made from several materials including foams, rubbers, and other materials, shaped to give the desired resistance to the $1^{st}$ wall 22. In another embodiment a spring is incorporated to provide said resistance to the displacement of wall 22 to recess 27.

The seal between the cover 12 and the pouch 14 can be any sealing means known in the art including a) superior surface contact b) liquid tight press fit, c) glue, d) adhesive surface, e) a seal or an O-ring, f) welding the pouch 14 to the cover 12 by one of the heat joint means known in the art, or g) any other sealing means known in the art. In some embodiments the cover 12 is part of the reservoir 14 sub-assembly. In some embodiments the cover 12 is sealed directly to the base 11 defining the pressure chamber 24 in between these two parts. FIG. 2d demonstrates a further preferred embodiment of the apparatus of the present invention comprising, in addition to the elements of embodiment 10, a membrane 29 and a spring 20 in a form of a washer spring. In this embodiment the pressure chamber 24 is defined between the cover 12 and the membrane 29. One advantage of this embodiment is the separation of parts to function which allow optimization of each part design and materials to its function. A further advantage of this embodiment is that the pouch is not constrained to the peripheral walls of the pressure chamber 24 there for the film walls see less and more even stresses. The embodiment of FIG. 2d comprises a resistance mechanism which prevents the pressurizing of the reservoir 14 before a defined pressure has been built in the pressure chamber 24. A semi-rigid concaved sheet-metal spring 20 is located between the pouch 14 and the membrane 29. Upon pressurizing the pressure chamber 24, said spring 20 absorbs the force delivered the force from the membrane 29 due to said pressure, preventing pressurizing of the reservoir. Upon a defined threshold pressure has been built in the pressure chamber, the spring collapses transferring the force generated by the pressure in the pressure chamber 24 to the reservoir 14, such that the reservoir experience an instant pressure buildup while the pressure in the pressure chamber can be built relatively slowly. The toggle spring 20 also provide a safety and compliance feature avoiding any possibility of the pouch 14 rupture under a defined pressure. It will be obvious to those skilled in the art. In further preferred embodiment of the present invention the spring 20 and the rubber seal 29 or attached to the pouch, or combined between the walls of the pouch 21 and 22, or combined between the layers of the film or foil that constitutes the walls. It will be obvious to those skilled in the art that other layers and components can be combined with the pouch in the fashion described above.

The pressurizing device of embodiment of FIG. 2d further comprises a pressure release device 36 for controlling the pressure in the pressure chamber 24. The pressure release device 36 controllably release excess pressure from the pressure chamber 24 to the surrounding ambient of to a further cell or cells, or channel or channels. The pressure release control means can include passive or active elements such as flow restrictors, pressure valves, or other fluid control means known in the art. Several pressure release devices are described in U.S. Pat. No. 6,258,063 and are incorporated here by reference.

The cover 12 is connected to the base 11 by one of the preferred means known in the art including glue or solvents, thread, screws, welding techniques, crimp, press fit, etc.

Preferred materials for the pouch walls include multi-layer films, incorporating PVC, PET, PE, PP aluminum lamination or deposition and can incorporate barrier layers, or can be made from thin metal foils or sheets such as SS, etc. The walls 21, and 22 can further incorporate other components over the wall layers or between the wall layers such as rubber sheet or sheet-metal. The pouch can further incorporate a filling port such as needle valve or a needless valve. The pouch can have rigid sections such as molded part or metal parts as long as at least part of the $1^{st}$ wall 22 can be ruptured by the rupturing means.

All of the above needle-free syringes have similar discharge characteristics: there is a high-pressure pulse during the first 1-5 ms of the injection, followed by a steady decay in liquid pressure over the remaining 80-160 ms. The peak liquid stagnation pressure arises from the impact of the ram against the piston at the start of the injection. Of all the devices tested, the Intraject device has the largest ratio of peak pressure (35 MPa) to average delivery pressure (6 MPa). Typical pressure regimes for needleless administration comprise an initial pick pressure typically around 30 MPA for efficiently penetrating the skin, immediately there after the pressure is dropped to lower values typically around 10 MPA. The pressure values vary from one apparatus to another and from one application to another and depend on the desired penetration depth and the orifice diameter. In addition, a review of accidents involving high-pressure liquid jets (Vijay 1989) and a review of needle-free injector designs (Maas and Brink 1987) detail the combinations of liquid pressures and jet diameters that have penetrated human skin. These data are useful for indicating the sufficient condition for penetration which in broad terms, suggest that a pressure of 15 MPa is sufficient for the perforation of human skin by a liquid jet of diameter in the range 0.1-0.5 mm.

The deliverable fluid 23 can be pressurized by applying pressure or force to the $2^{nd}$ wall 21 either by pressurizing the pressure chamber 24 or by introducing a mean for delivering force to the $2^{nd}$ wall 21 of the pouch 14.

Force delivering means include any mechanical means that can deliver force to the reservoir wall. Such mechanical means can be actuated by electric means, hydraulic or pneumatic actuators, a spring of any fashion, or by other actuation means known in the art. For applications which have lower pressure requirements (will be presented in following figures) manual pressure can be applied to the $2^{nd}$ wall 21 for example by directly or indirectly pressing with a finger as exemplified in FIGS. 15-17.

The pressure chamber of the pressurizing device can be pressurized by one or more internal or external pressure sources or generators. The pressurizing of the pressure chamber can be gradually or instant. Alternative External pressure sources will be introduced via the pressure port 13 and can be one or more of the pressure sources (compressible or non-compressible) known in the art including: a) a compressible fluid pressure booster, b) non-compressible fluid booster, c) an electric pump, d) a manually operated pump, e) a foot pump, e) a chemical reaction, f) a change of physical phase of a substance g) heating of a substance, etc.

Alternative internal pressurizing sources include the means listed above for the external pressure source and the means listed in the prior art or that are known in the art.

In one embodiment the internal pressurizing means comprises a controlled chemical reaction between two reagents which are kept separately in the pressure chamber 24 and upon an activation action are brought in contact which initiate a gas generating chemical reaction. Preferred reagents can be Sodium Bicarbonate (baking powder) and Citric Acid, the reaction of which generates Carbon Dioxide. The reagents or at least one of the reagents can be kept in a dedicated blister which upon the activation action is pieced. In one embodiment one reagent is set as loose powder in the pressure chamber 24 and the second reagent is introduced through a resealable port into the pressure chamber 24.

In another preferred embodiment the internal pressurizing device comprises an electrolyses system comprising electrolyte, and electrodes and activation circuitry. The arrangement being such that the electrolyses reaction on at least one of the electrodes generate gas. An example of a gas generating electrolyses reaction is presented in U.S. Pat. No. 6,530,900 incorporated here by reference. In a particular case the electrolysis arrangement is a fuel-cell and the gasses are generated either in the fuel compartment or in the cell. In a further embodiment the electrolysis arrangement is a battery cell and the gas is generated during a discharge of the battery.

In another preferred embodiment the internal pressurizing device comprises is a combustible substance that will be ignited by spark or heat. Several alternatives of such pressurizing devices are described in the prior art including one describing an explosion process and one that describes a more controllable combustion.

Another preferred internal pressurizing device comprises a substance or substances in supercritical state that will react or change phase upon providing activation energy by a mechanical snap of a spring.

In some embodiments of the present invention at least part of the pressurizing device is incorporated in the reservoir 14 assembly. In one embodiment the reservoir assembly comprises at least one additional pouch for storing reagents for the chemical reaction that will pressurize the pressure chamber 24. In one embodiment the reagent will be exposed to a second reagent by external manipulation that will breach said compartment. In another embodiment the reservoir assembly comprises at least one pressure channel. In a further embodiment the reservoir assembly comprises at least part of the electronic or electric circuitry of the pressurizing device.

The above pressurizing activations can be triggered by various means and synchronized with various events. In one embodiment the activation occurs upon screwing the cover 12 on the apparatus.

Typically a needleless hypodermic administration means will incorporate one or more orifices having a diameter in the range of 0.3 mm, and typical pressure for intradermal delivery is in the range of 30 MPa. It is sometimes beneficial to form a pressure curve during the delivery starting with a higher pressure (10-30 MPa) that facilitate the penetration of the skin following by a lower pressure for the duration of the delivery. The pressure in the pouch curve can be controlled by several parameters including: a) the pressure in the pressure cell 24, b) the volume of the pressure cell, c) the volume of the gas in fluid contact with the pressure cell 14, d) any flow or pressure controlled devices introduced in the pressure port 13 such as a flow restrictor, e) the nature of the pressure generator means, f) pressure release ports or ventilation ports that lead the pressure cell 24 to the surrounding ambient or to a further cell, g) the collapsing nature of a structural member [such as the spring 20 describes in FIG. 2d] that supports the pouch.

Typical volume of the deliverable fluid for needless injection applications is 0.5 ml-1.0 ml.

Various administration devices can be incorporated with the apparatus including a hypodermic needle or needles, a micro-needle or micro-needles, a tube.

Activation of an internal pressurizing means can include a press of a knob, a quarter turn of the cover 12, shaking the apparatus or impacting, heating, etc.

The pouch can be factory prefilled, or filled prior to use through a dedicated filling port.

The pouch can be maintained in the apparatus or introduced into the apparatus prior to use.

In some embodiments the apparatus of the present invention includes an anti-abuse mechanism to avoid extraction of deliverable fluids form the device after the administration has been completed, said anti-abuse mechanism can provide one of the following actions: a) depressurizing the pouch, b) sealing the outlet port, c) removing the outlet port from the surface of the apparatus, d) preventing access to the outlet port, e) disconnecting the outlet channel 26 from the outlet port, or f) any other anti-abuse means known in the art.

The cover 12 is preferably made sheet metal, rigid plastic, flexible film or foil, or the combination of the formers. In one embodiment the cover is merely a film layer incorporated in the film assembly confining the reservoir there under. In a yet further embodiment the cover confined additional capsules for ingredients associated with the rupturing mechanism.

The base 11 is preferably made from sheet metal or molded plastic or combination of the two.

The rupturing member 25 is preferably made from stainless steel or rigid plastic needle. In the later case the rupturing member can be molded or co-molded or insert molded as part of the base. In the case of rupturing member 25 made from metal it can be insert molded with the molded plastic base.

The conduit 26 preferably has a uniform diameter or a variable diameter ending with the diameter required for the administration means. Prior art U.S. Pat. No. 6,258,063 describe specific preferred orifice profiles incorporated here by reference.

The surface of the base adjacent to the skin is preferably shaped such that the contact between the orifice 28 and the skin is improved and the skin is slightly stretched when the apparatus 10 is attached to the skin.

In a further preferred embodiment the apparatus 10 incorporates mechanical indication means to communicate with the patient or the care giver or a further device, certain conditions of the apparatus such as: that the pouch is pressurized and/or indication that the delivery has completed.

The space between the pouch 14 and the base 11 is ventilated (for example via ventilation channels) such that that the pouch can be well accommodated on the base 11, preventing leaks of the deliverable fluid between the pouch 14 and the base 11.

In the embodiment of FIG. 2 a dead space exist between the pouch 14 and the administration means 28, including in the recess 27. To avoid delivery of air that could present in said dead-space, the dead space can be filled with inert fluids or active-therapeutic fluids such as sanitizing substance in the form of liquid, gel, or paste. At the pressurizing stage of the pouch 14 said dead-space filler will advance into the administration means and replace presented gasses. In the case where the administration means is a needless jet orifice, the dead-space filler substance will spread around the drug penetration point prior to the deliverable fluid penetration of the skin. In a further preferred embodiment the pouch wall 22 includes a sealing layer that can seal onto the penetration member 25 such that upon rupturing the pouch wall 22, the wall will seal around the rupturing member such that the fluid is limited to advance only into the conduit 26 and can not access the recess 27, therefore avoiding leaks or mixing of air or gas presented in recess 27 with the deliverable fluid. Such a sealing arrangement can be achieved by incorporating a rubber or compressed rubber (in a septum fashion) between the layers of the wall 22. The rupturing member 25 in this case is preferably thin and made for easy penetration through the wall 22, and the arrangement is such that the penetration of the rupturing member continues after the instant of rupturing the wall 22.

In a yet another embodiment the pressurizing device is such that the pressure in the reservoir 14 drops toward the end of the dose administration causing the portion of the wall 22 that was stretched into recess 27 to shrink back and in return retract the ruptured portion of wall 22 away from the rupturing member. Thus when the reservoir 14 is about to empty and the $2^{nd}$ wall 21 is reaching the $1^{st}$ wall 22, there is no risk that the $2^{nd}$ wall 21 will be damaged by the rupturing member and therefore the stopper 39 can be avoided.

Figure 2E:
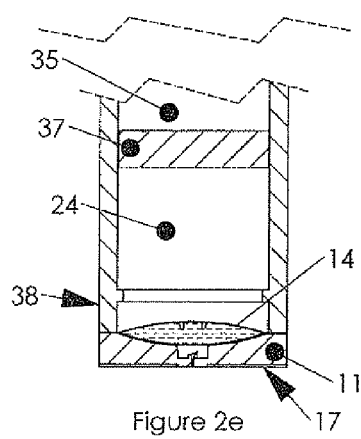
Figure 2C:
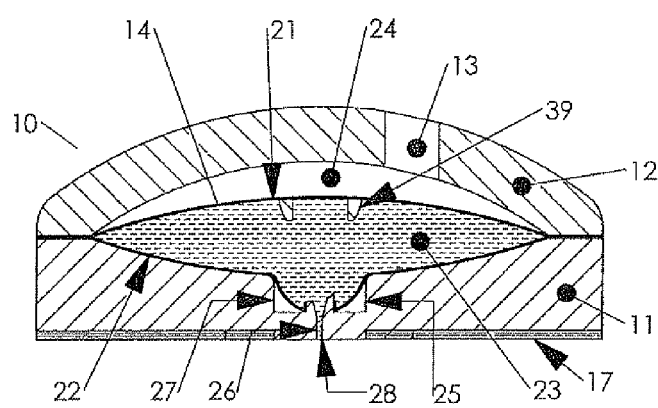

FIG. 2e presents a yet another embodiment of the apparatus of the present invention in which the pressure chamber 24 is completed by a cylinder 38 and a piston 37 which present a displaceable fluid barrier between the fluid in the pressure chamber 24 and the rest of the pressurizing device. The fluid in the pressure chamber 24 may be a compressible fluid or a non-compressible fluid. Pressure chamber 24 is pressurized by displacing the piston 37 downward. In one embodiment piston 37 is urged downward by pressure applied to the area above the piston 35. In another embodiment the piston 37 is urged downward by mechanical force, said force can be applied by any means known in the art including electric solenoid actuator, magnetic actuator, electric motor, or direct finger pressure. In yet another embodiment the piston 37 is connected with a pressure amplification arrangement. In one embodiment the piston 37 is part of the disposable portion of the device. In another embodiment the piston 37 is part of a permanent system to which the disposable apparatus is assembled. In one embodiment the cylinder 38 is part of the disposable portion of the device. In another embodiment the cylinder 38 is part of a permanent system to which the disposable apparatus is assembled.

Figure 3A:
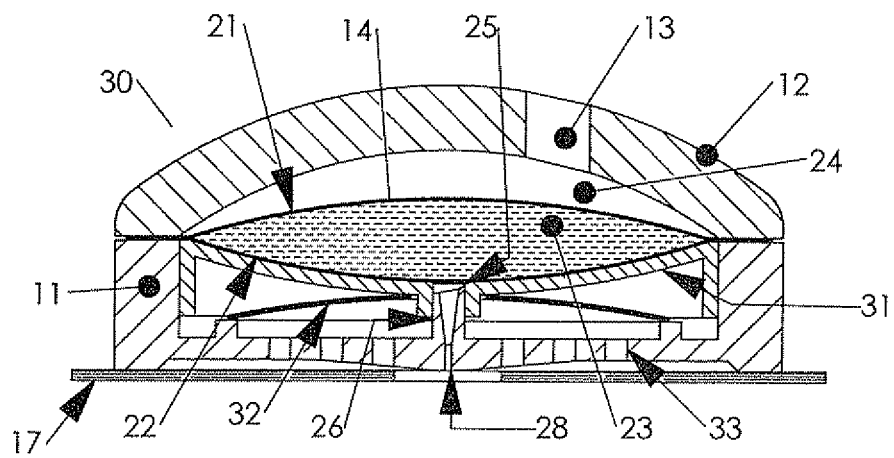
FIG. 3 presents section views at various operational positions of a second preferred needleless patch embodiment of the drug delivery apparatus of the present invention comprising a moving plate.
Figure 3B:
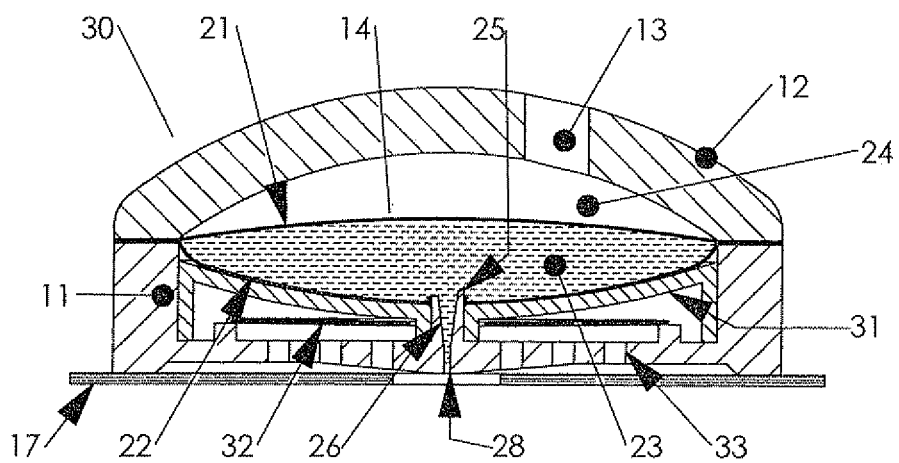
Figure 5A:
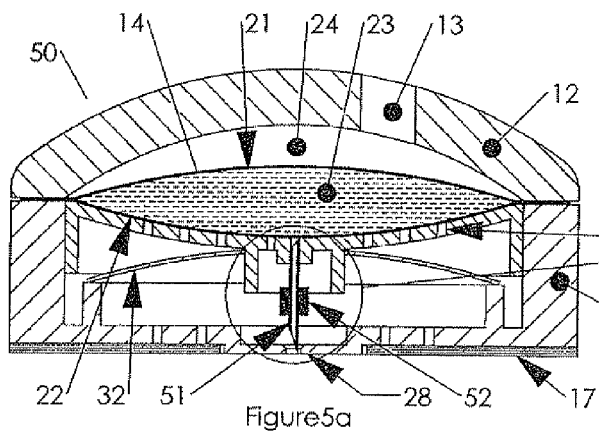
FIG. 5 presents another embodiment comprising a hypodermic needle administration device where said needle also provides the rupturing member.
Figure 5B:
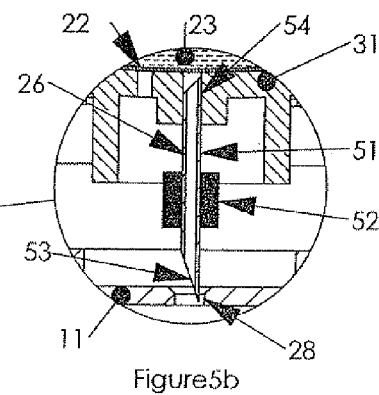
Figure 5C:
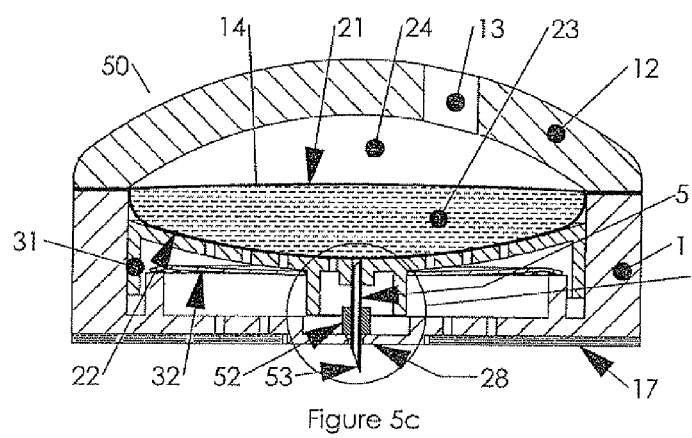
Figure 5D:
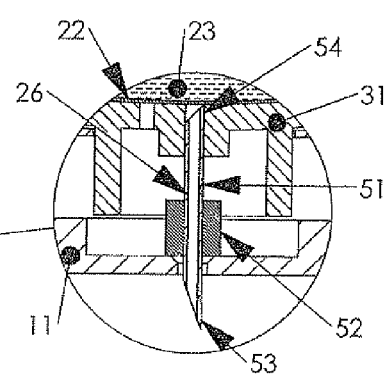
Figure 5E:
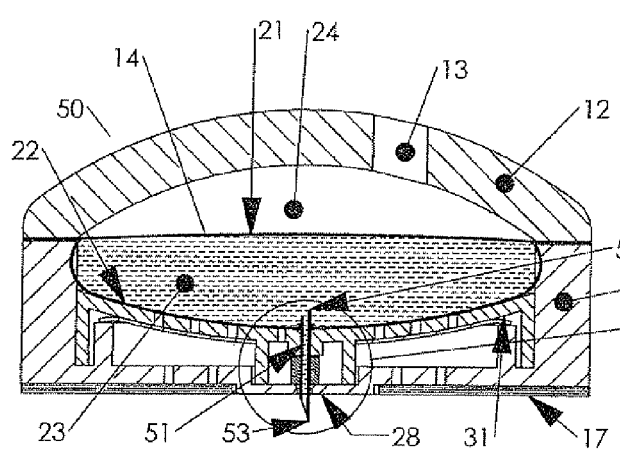
Figure 5F:
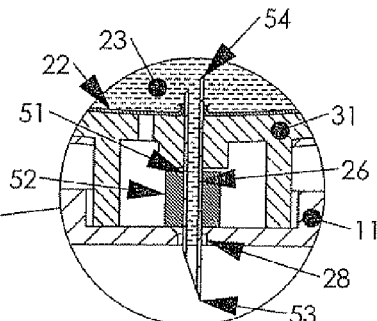

FIG. 3 presents a further preferred needless injector patch embodiment 30 of the present invention in which the recess 27 of embodiment 10 is eliminated and therefore the deadspace referred to in the description of FIG. 2 is minimized. Embodiment 30 comprises a different rupture-control mechanism than the one of embodiment 10 which will be described here under. FIG. 3a demonstrates the rest position of the apparatus 30 in which the reservoir 14 is not pressurized. The recess 27 of the apparatus 10 demonstrated in FIG. 2 is eliminated. In this embodiment the pouch 14 is accommodated on a moving plate 31 having a central opening for receiving the penetration member 25 and the fluid conduit 26. The moving plate 31 is supported by a spring 32 in a form of a disc (washer) spring which biases the moving plate 31 away from the penetration member 25. The spring 32 is capable of absorbing some loads from the moving plate 31 with relatively small deflections, but at a certain threshold load the spring will collapse in what is referred to as a toggle effect, in which state the spring will enable large displacement of the moving plate under relatively smaller loads. In some spring designs the toggle effect is such that the spring 32 will actually urge the displacement of the moving plate 31. Thus, when the pressurizing device pressurizes the reservoir 14, the reservoir 14 pushes against the moving plate 31 causing resulting in none to relatively small displacement of the moving plate 31, until a threshold pressure in the reservoir deliver the threshold force to the spring 32 which in returns collapses causing a snap displacement of the moving plate 31 toward the rupturing member 25, resulting in an instant penetration of the rupturing means into the pouch, as shown in FIG. 3b. Upon rupturing of the reservoir 14 the deliverable fluid expels from the reservoir 14 and through the fluid conduit 26 and the administration device 28 and into the skin of the patient. A rupture-control mechanism is demonstrated above, where the reservoir is ruptured in a snap action when the reservoir is pressurized to a defined pressure, regardless of the nature of the pressurizing means. The area between the $1^{st}$ wall 22, and the base 11 and the moving plate 31, is ventilated such that the pouch can be well accommodated in place such that a sealed connection is formed and the deliverable fluid 23 is limited to advance to the fluid conduit 26. Holes 33 allows the space under the pouch 14 to ventilate enabling the displacement of the pouch 14 and the moving plate 31 with out building pressure in that space.

At the end of the administration, as the pressure or force that was applied to the pouch 14 is removed, the spring 32 biases the moving plate 31 to retract, disconnection the fluid conduit 26 from the pouch 14, which prevents leaks or abuse of the deliverable substance 23.

In other preferred embodiments when the moving plate 31 advance to the rupturing position it opens an exhaust channel from pressure chamber 24 which at the initial position was sealed between the base 11 and the moving plate 31. The exhaust channel can lead to the surrounding ambient or a further chamber or chambers, directly or through flow/pressure control devices. Examples of such are described in the prior art U.S. Pat. No. 6,258,063.

In another embodiment a different rupturing-control mechanism is implemented where the movement of the moving plate 31 is eliminated up until a defined threshold pressure has been built in the reservoir, by incorporating a mechanical interference between the moving plate 31 and the base 11 which yield under a defined threshold force. An example of a mechanical interference is a lateral protrusion in the base 11 on the sliding surface of moving plate 31.

Several alternative biasing means can be applied in place of the washer spring 32 including a coil spring, a cantilever spring, a flexible integral lateral extension to the moving plate 31, or any other biasing means known in the art.

Referring now to FIG. 4 a further preferred patch embodiment of the present invention is demonstrated, in which the administration device of the apparatus 40 is a hypodermic needle 41. The apparatus of embodiment 40 comprises a rupture-control mechanism, and auto-insertion mechanism of the needle as described here under. The needle 41 has a first sharpened end 44 facing the pouch 14—being the rupturing means—and a second sharpened end 45 facing an opening 42 in the base 11 for penetrating the skin. The needle 41 is fixed to the moving plate 31, such that (as demonstrated in FIGS. 4a and 4b) when the pressure in the pouch exceeds a defined threshold the moving plate 31 snaps toward the base 11 (in a similar actuation fashion of the moving plate of embodiment 30) causing the penetrating end 45 of the needle 41 to extend through the opening 42 in the base 11 and penetrate the skin of the patient, as demonstrated in FIG. 4c. An auto insertion mechanism has been demonstrated. Following, as demonstrated in FIGS. 4d and 4e, the pressure in the pouch continues to rise causing the wall 22 of the pouch 14 to stretch and extend toward the rupturing means 44 and eventually rupture when a contact is achieved similar to the rupture-control mechanism of embodiment 10.

Upon depressurizing the pouch 14 the moving plate 31 retracts to the rest position pulling the needle 41 out of the skin and into the apparatus 40, thus: a) preventing accidental sticking, and b) preventing abuse of the apparatus, c) preventing leaks, and d) minimizing the presence time of the needle in the patient body. Several enhancement can be incorporated for further anti-abuse protection including: a) locking the moving plate 31 at the retracted position, b) disengagement of the rupturing means 44 from the pouch 14 and where the pouch 14 is made such that it seals the penetration point, c) sealing on the hole 42 in the base 11 after the needle 41 has retracted, and d) other abuse preventing means known in the art.

In a further embodiment the administration device comprises more than one needle. In a yet further embodiment the administration device comprises a micro-needle or needles which are auto inserted.

FIG. 4 also demonstrates the ventilation means 46 described in the text of the previous figures that allows the space between the pouch 14 and the base 11 to ventilate.

In some embodiments a flow regulating mechanism or pressure regulating mechanism is implemented in the fluid passage between the reservoir and the administration device, said fluid control mechanism regulates the administration rate or other characteristics of the deliverable fluid. In one such embodiment the regulating mechanism is implemented in the exit of the reservoir. In another such embodiment the regulating mechanism is implemented in the administration device for example inside a needle or micro-needle.

Referring now to FIG. 5, a further preferred embodiment 50 of the patch apparatus of the present invention is demonstrated where the administration device is a needle. Like the apparatus of embodiment 40, the apparatus of the present embodiment 50 comprises a moving plate, but in this embodiment the recess 27 of embodiment 40 is eliminated. The rupture-control mechanism of the present embodiment 50 is similar to that of embodiment 30 of FIG. 3—moving Plate 31 comprises a central opening for receiving the penetration member 25 and the fluid conduit 26 in a form of a needle. The needle 51 comprises a first end 54 facing the pouch 14—being the rupturing means—and a second end 53 facing the opening 28 in the base 11 being the penetration end. A lateral feature 52 is fixed to the needle forming a rigid needle assembly which is in fluid-tight frictional connection with the moving plate 31. FIGS. 5a and 5b demonstrates the rest position where the tip of the needle 53 is housed in the base 11 and the rupturing means 54 is set in distance of the pouch 14. Upon exceeding a threshold pressure in the pouch the retaining force of the spring 32 is overcome and the moving plate snaps toward the base 11 causing the end of the needle 53 extend from the opening 28 in the base 11 and penetrate the skin, to the point that the lateral feature 52 reaches the base 11 as demonstrated in FIGS. 5c and 5d. FIGS. 5e and 5f demonstrates the following step where the needle is stopped and the pressure of the fluid 23 in the pouch 14 keeps forcing the moving plate 31 toward the base 11, and causing the needle 51 to slide and penetrate the pouch 14. Upon depressurizing the pouch 14 the spring 32 retracts the moving plate 31 retracting the needle back into the apparatus 50. It will be obvious to those skilled in the art that the frictional detention means of the needle 51 to the moving plate 31 can be replaced by various other means known in the art including: a) a bellows having one side sealed on the needle 51 and a second end sealed on the moving plate 31, b) a mechanical interference, or c) any other means known in the art.

The advantages of administrating the drug via a penetrating needle include 1) avoiding misfiring into the skin in which case in several occasions the skin is injured by the misdirected jet, 2) reduce the pressures required for delivering the drug as the initial penetration of the skin requires a high pressure pick.

Reducing the deliverable pressure has several advantages. One advantage is that the parts of the apparatus that are exposed to the pressure can be made with thinner walls or from weaker materials which have an effect on manufacturing costs. The same applies for the joint structure between the parts that are exposed to pressure which are preferably exposed to lower forces. Another advantage is that more options for propelling the drugs exist when the pressure requirement are lower. For example the pressure that can be achieved with Carbon Dioxide gas at room temperature do not exceed 10 MPa, and therefore apparatuses that use Carbon Dioxide propellant incorporate an amplifying mechanism which delivers higher pressure to the drug reservoir. Such mechanisms add to the cost of the e. The penetration member can be relatively short and its length does not have to exceed the length that secure the initial penetration of the skin. It will be obvious to those skilled in the art that alternatively to the needle demonstrated in FIG. 4, the administration means can be a plurality of needles, a micro needle, or micro needles.

In some embodiment the propelling pressure is in a form of pressure pulses applied by a pressure pulsation generator. The pressure pulse generator is constructed such, and positioned such that the pulse it generates effectively advance the fluid toward and in the conduit. Preferred pressure pulse generators include transducer elements and electro-hydraulic sources. For the purposes of the present invention, "transducing element" refers to any structure that exhibits a mechanical force or strain when subjected to an applied electrical stimulus. Examples of transducing elements may include layers of piezoelectric material, piezoresistive materials, electrically conductive materials, magnetostrictive materials, magnetoresistive materials, etc. Electro-hydraulic pulse generator refers to pulse generators where an electrical spark is created in water or other suitable liquids and a pulse of electricity at high peak power is passed through the spark. This forms rapidly expanding plasma in the water that creates a shock wave. Examples of applications of Electro-hydraulic pressure pulses are exercised by Tetra-Corporation Albuquerque, N. Mex. The pressure wave from the pressure pulse generator is controlled such that it is directed and focused to the fluid conduit causing the deliverable fluid to be expelled from the reservoir in small discrete incremental metes. In further embodiments the pressure pulses are superimposed on a (none-pulsating) base pressure in the reservoir provided by one of the pressurizing means discussed above. Thus the pressure pulses increase the rate in which the deliverable fluid 23 would be expelled by merely the base pressure. In another embodiment a restrictor is located in the delivered fluid 23 passage to the administration device, said restrictor prevent flow to the administration device under a defined pressure threshold. The restrictor threshold pressure is set higher than the base pressure and lower than the super-positioned pick pressure pulses from the pulse generator, therefore the expelled fluid amount is relative to said pressure pulses—form, frequency, amplitude, etc. Thus this embodiment provides means for controlling the delivery rate of the deliverable fluid and for a closed loop control. Examples of applicable flow restrictors include: a) a mechanical pressure release valve, and b) a hydrophobic membrane or mesh which that can resist fluid passage under a threshold pressure. With this arrangement the apparatus is suitable for controlled slow release delivery of drugs. In some embodiments the pulsation generator is incorporated in the walls of the reservoir, either attached to the wall from the inside of the reservoir or the external side to the reservoir, or it is incorporated with in the wall for example between the layers of a film wall. In other embodiments the pulsation generator is incorporated on the walls of the pressure chamber. In this case the fluid in the pressure chamber 24 is of a kind that efficiently communicates the pressure pulses to the reservoir walls, and it is preferably a liquid such as water or saline. The electronic circuitry that operates the pulse generator can be integrated with pulse generator. Suitable power source and circuitry for integrating into or onto a thin film is described in U.S. Pat. No. 6,906,436 incorporated here by reference. Activation means for the pulse generator include any activation means known in the art. Examples for activation means are demonstrated in U.S. Pat. No. 6,805,998. In one embodiment the activation mean of the pulsation device is the presence of a threshold base pressure, thus when the reservoir is pressurized to said pressure threshold value, the pulse generation is initiated. In another embodiment more than one pulse generator is incorporated.

In some embodiments the arrangement is such that the drug pulsation causes the administrating needle to pulsate which enhance the penetration of the drug to the tissue as proposed by U.S. Pat. No. 6,743,211 incorporated here by reference.

It will be obvious to those skilled in the art that alternative rupture-control mechanisms can be implemented in place of the friction mechanism between the needle 51 and the moving plate 31. For example the $1^{st}$ wall 22 of the pouch 14 can be designed to resist the penetration of the rupturing member 25 until a threshold force has been achieved.

In some embodiments the sealing between the needle 51 and the moving plate 31 is achieved using a bellows component having a first open end connected in sealed fashion to the moving plate 31 and a second open end connected to the needle 51 in a sealed fashion. The bellows allows for relative motion between the moving plate 31 and the needle 51 during the rupturing step, while keeping a tight fluid connection between the reservoir 14 and the administration means 28.

Figure 6A:
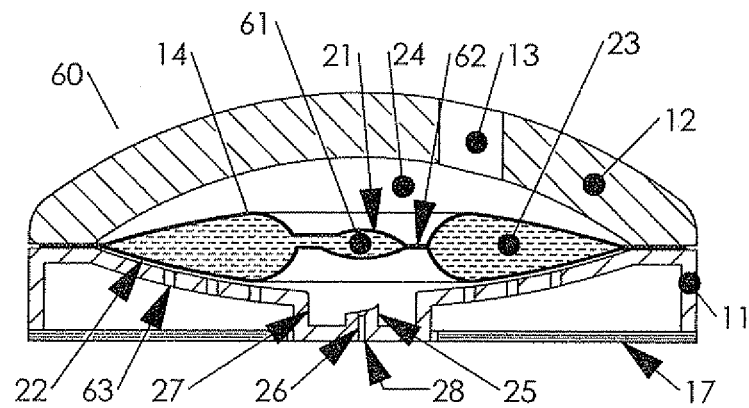
FIG. 6 presents various section views of a further preferred patch embodiment of the present drug delivery apparatus of the present invention where demonstrating a different concept of the rupture-control mechanism.
Figure 6B:
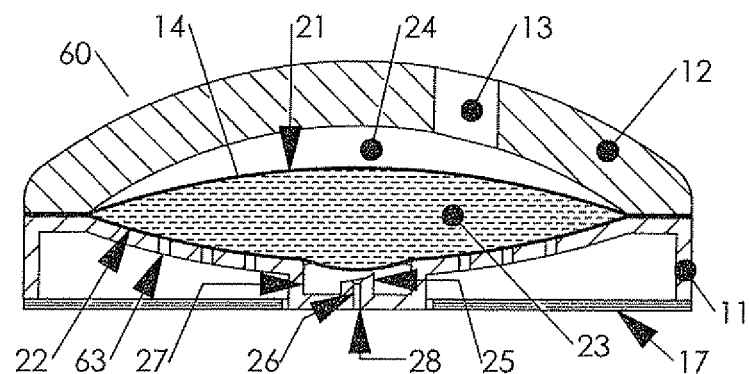
Figure 6C:
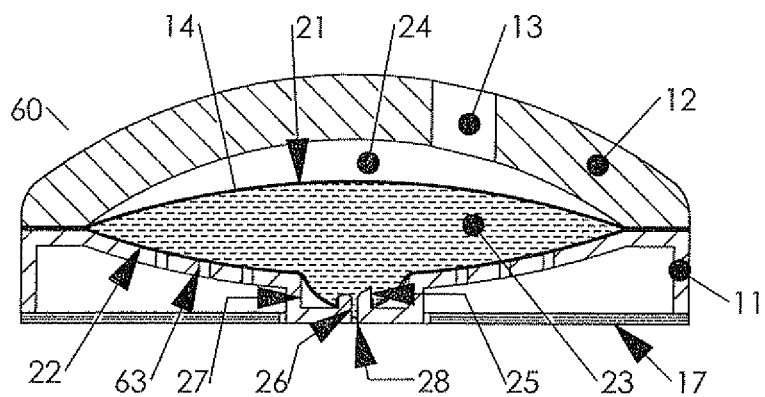

Referring now to FIG. 6, a further preferred embodiment of the present invention is demonstrated where the apparatus 60 comprises a yet another rupture-control mechanism. In this embodiment a particular welding geometry of the pouch 14 prevents the wall 22 from extending and reaching the rupturing member 25. The welding area 62 is a relatively weak welding which is separated under a defined pressure in at least one of the reservoir's compartments. Upon pressurizing the pouch 14 the weakened welding section 62 is separated allowing the wall 22 of the pouch 14 to reach the rupturing member 14. The ventilations holes 63 prevent pressure to be built between the pouch 14 and the base 11 which could interfere with the separation of the welding 62. Note that the peripheral welding of the pouch which compose a barrier to the drug from the surrounding is not at separation risk even if it had not been clamped between the cover 12 and the base 11, as the pressure in the reservoir and in the pressure chamber are similar. It will be obvious to those skilled in the art that other rupture-control means could be incorporated to keep the rupturable portion of the wall 22 away from the rupturing mean, including: a) gluing wall 21 to 22, b) forming reciprocal featured in wall 21 and 22 that mechanically engage with each other, c) attach a feature to at least one of said walls that will interfere with a reciprocal engagement means in the other wall, d) any other means know in the art.

Referring now to FIG. 7, a further preferred embodiment of the present invention is demonstrated where the pouch incorporates two compartments 23 and 71 separated by an annular separateable welding area 62. In one embodiment, upon pressurizing at least one compartment of the pouch 14, the weakened seal area 62 separates causing the two substances to mix prior to rupturing the pouch. The compartments can be used to hold two different substances that have a limited shelf life when are brought together that need to be mixed prior to administration. The substance in compartment 71 can take several forms including a liquid, a gel, a paste, a solid, a lyophilized cake, a powder, or a combination of the above. In a further embodiment the structure remains mostly the same but the weakened welding area 62 is stronger thus the rupturing of compartment 71 takes place prior to the separation of the weakened sealing area 62, such that one substance is delivered prior to the second substance. The sequential delivery is advantageous when the substances should not be mixed or are restricted to that by regulation. In a further preferred embodiment the pouch is separated to more than two compartments which will separated at a desired sequence by controlling the welding strength and shape. In a further embodiment the reservoir comprise more than two compartments of deliverable ingredients and the delivery procedure combines mixing of at least two compartments and sequential delivery of at least two compartments. In one embodiment the activation of the mixing does not necessarily have to be engaged with the mechanism that pressurizes the pouch for the purpose of delivering the deliverable fluid. Instead secondary operation can activate the mixing such as: a) manipulating a mechanical member that will squeeze one compartment into the other or b) have it done directly with the fingers when the cover 12 is removed, or c) by any other means known in the art. The embodiment described above is suitable for combination drug delivery, or for reconstitution (resuscitation) of deliverable pharmaceutical agent. Manual mixing of the reservoir's compartments is exemplified in FIGS. 15-17.

In a further embodiment the mixing of the chambers is performed manually by squeezing at least one compartment thereby pressurizing the compartment which separates the seal to the at least one other compartment. In a further embodiment the fluid communication of the fluids from the reservoir with the administration device is controlled by a valve or a shut-off which will be opened after the substances of the different compartments has been mixed.

FIG. 7b demonstrates the embodiment 70 at an intermediate stage of pressurizing the reservoir. The pressure 24 is applied to the wall 21 which pressurizes the deliverable fluid 23 which in turn (since recess 27 is not pressurized) cause walls joint 62 to separate and allows the ingredient of compartment 71 to mix with the deliverable fluid 23.

Referring now to FIGS. 7c to 7e a further embodiment of the present invention is demonstrates where the multi compartment reservoir 14 assembly further comprises a flow conduit 78 which is separated by a sealed separable joint 79 from the deliverable fluid compartment 71. Conduit 78 leads to the administration device 28—in a form of hypodermic needle—via fluid conduit 26. The separable sealed joint 79 will separate under the presence of a threshold pressure value which is higher than the pressure threshold required for separating the joint 62. A drug delivery apparatus that utilize a separable sealed joint between a deliverable fluid reservoir and an administration needle, and a method for manufacturing said apparatus is described in U.S. Pat. No. 4,955,871 incorporates here by reference.

FIG. 7c demonstrates the rest position of this embodiment, where the pressure chamber 24 is not pressurized, showing a first compartment containing the deliverable fluid 23 and the second compartment 71. U.S. Pat. No. 4,955,871 also provide a method for filling a pouch fashion reservoir, incorporated here by reference.

FIG. 7d demonstrates the embodiment where a first pressure threshold has been achieved which cause the two compartments to merge and the deliverable ingredients to mix.

FIG. 7e demonstrates the embodiment where a second pressure threshold has been achieved higher than the first pressure threshold which cause the joint 78 to separate establishing a fluid connection between the deliverable fluid and the administration device.

In one embodiment the fluid conduit 78 further comprises a flow control mechanism or a pressure control mechanism to control the rate or other properties in which the deliverable fluid is delivered to the body of the subject. In another embodiment the fluid conduit comprises a non-return valve for preventing flow into the reservoir.

In another embodiment the reservoir assembly 14 comprises more than one fluid conduit leading from one compartment to several administration devices.

In another embodiment the reservoir assembly 14 comprises more than one fluid conduit leading from different compartments to a common administration device.

In another embodiment the reservoir assembly 14 comprises more than one fluid conduit each connecting a specific compartment with a corresponding administration device.

In one embodiment a mixing element is implemented in the conduit 78 to enhance the mixing of the ingredients of the deliverable ingredients.

In another embodiment the rupture of the wall leading to the conduit is performed by a rupturing member. In another embodiment said rupturing member confine the conduit as demonstrated in the embodiments demonstrated in U.S. Pat. No. 4,955,871 incorporated here by reference.

In another embodiment the merging of the two compartments is achieved by manually pressurizing at least one of said compartments and the administration of the fluid of the mixed substance is provided by manually pressurizing the merged compartment, after constituting a fluid communication between the merged compartment and the administration device as exemplified in FIGS. 15-17. The assembly of the drug administration device in such case can be reduced to merely a multi-compartment film assembly and an administration device.

The multi-compartment pouch of FIG. 7 can be filled by various techniques known in the art including form-fill-seal technologies the different compartment can be filled in the same filling machine or be transferred to different machines to perform the various filling stages. Several filling techniques are described in U.S. Pat. No. 6,258,063 including means for reducing or eliminate air bubbles, and are incorporated here by reference. Another applicable filling approach for the multi-compartment pouch of the embodiment of FIG. 7 is describes in US Pat. Application 20040240324 incorporated here by reference. This patent application presents a chemical time indicator construction where an ink compartment is isolated from a migration media until the time of activation. US Pat. Application 20040240324 proposes a "sandwich" construction where the liquid compartment is formed between a first film layer and a second film layer prior to filling said ink compartment, leaving an inlet and ventilation holes for said compartment in the surface of the second film layer. A third film layer is applied after the compartment has been filled and seals the inlet and ventilation ports. This last sealing has weakened areas that rupture under pressure to constitute fluid communication between said ink compartment and an adjacent compartment. For the purpose of the present invention the implementation of the above described construction is such that the compartments will contain the pharmaceutical ingredients to be mixed and the mixture will occur upon pressurizing one of the compartments.

It will be obvious to those skilled in the art that that the multi-compartment pouch is not limited to the co-annular structure presented in FIG. 7 and that the compartments can be arranged side by side, opposite to each other on a common substrate, remotely from each other having a channel directing the fluids from one compartment to the other, or other.

The weakened separable seal joints can be achieved by controlling the welding or gluing properties of this section. In one embodiment the weakened area is printed with a material, e.g. paint, which forms a weak adhesive bond with the thermal adhesive which may be W60 and W60 pre-applied aliphatic polyester water-based urethane adhesives from Lmarr (Glen Ellen, Calif., US).

Figure 8A:
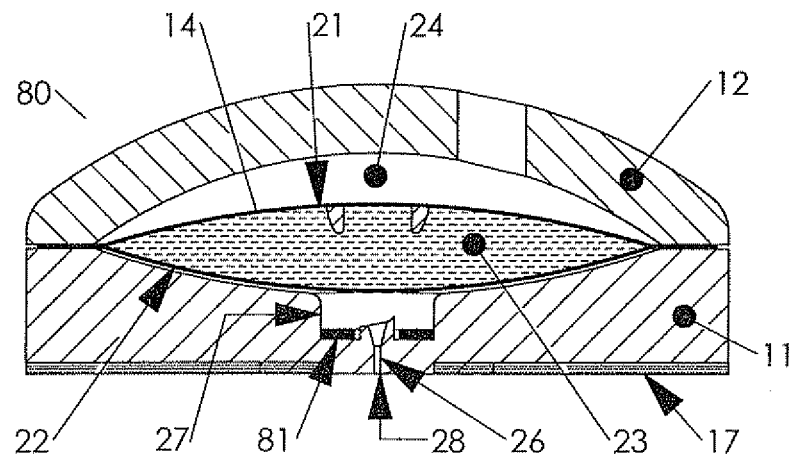
FIG. 8 presents a further preferred patch embodiment of the present invention where the fluid in the pouch mixes with a second substance upon rupturing said pouch.
Figure 8B:
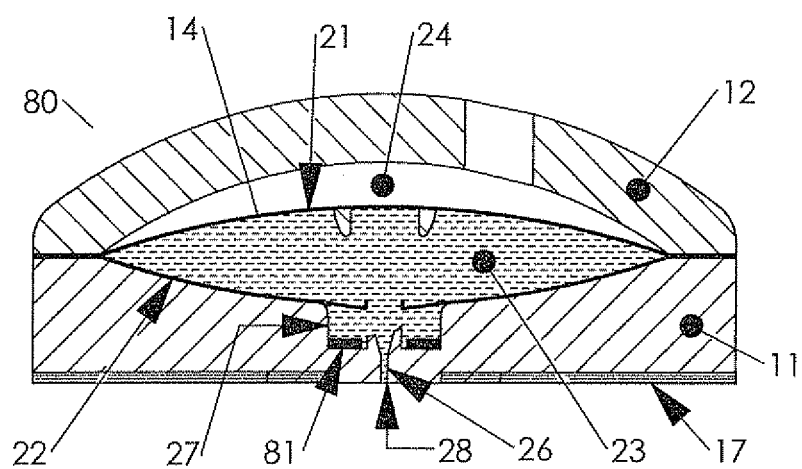

Referring now to FIG. 8 a further preferred embodiment 80 of the present invention is demonstrated, which like embodiment 70 incorporates a second deliverable ingredient 81 to be mixed and delivered with the deliverable fluid 23 contained in the pouch 14. Ingredient 81 is accommodated in recess 27 and may be a solid substance, a loose or compressed powder, a liquid, gel or paste, or in any other for known in the art. Upon rupturing the pouch the pressurized stream of the fluid 23 mix or erodes substance 81 and carry it through the fluid conduit 26 to the administration means 28. The deliverable fluid 23 in the pouch 14 can be a liquid or gas depending on the application. In order for the deliverable liquid 23 to penetrate into recess 27 the seal between the rupturing member 26 and the wall 22 has to be prevented (in oppose to the requirement in previous embodiments). This achieved by the controlling the pressure regime in the reservoir which prevents the stretchable portion of the $1^{st}$ wall 22 from stretching to a full contact with the rupturing device 25. FIG. 8b demonstrates the embodiment 80 after the pouch 14 has been ruptured. It will be obvious to those skilled in the art that the deliverable ingredient 81 can be accommodated in several locations along the fluid passage from the reservoir 14 to the administration device. In one embodiment ingredient 81 is accommodated on the external side of the reservoir $1^{st}$ wall 22. In another embodiment the ingredient 81 is accommodates in or on the administration device such as inside a needle or micro needle or on the external penetrating surface of those. Different form of incorporating a pharmaceutical ingredient in the flow passage of a liquid deliverable ingredient from a reservoir to the body are presented by U.S. Pat. No. 6,656,147 incorporated here by reference.

In a yet another embodiment the second substance is encapsulated in a compartment that is integral to the reservoir 14 and sealed from the rest of the device. In which case two rupturing events will occur: a first rupture will connect the deliverable fluid 23 of the reservoir 14 with said compartment, causing the substances to mix, while the second rupture will connect the merged volume with the fluid conduit. The substance 81 can be integrated in a mesh that is positioned between most of the merged volume and the fluid conduit 26 such that the deliverable fluid 23 will flow through the mesh and wash substance 81 off it.

Figure 9A:
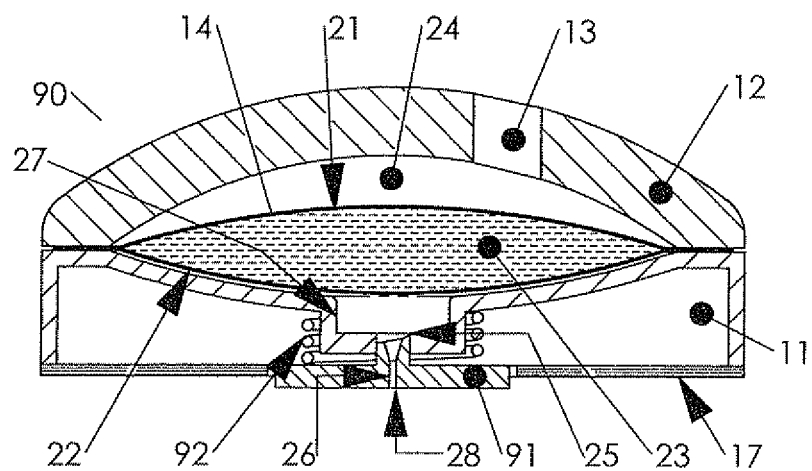
FIG. 9 presents a further preferred embodiment of the present invention comprising a safety catch.
Figure 9B:
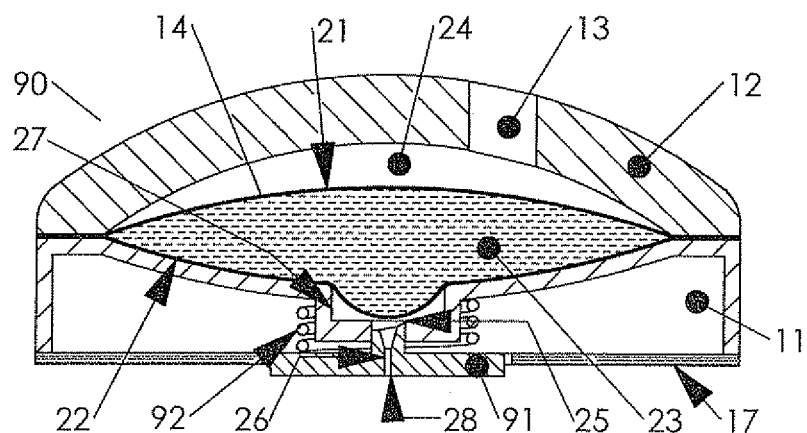
Figure 9C:
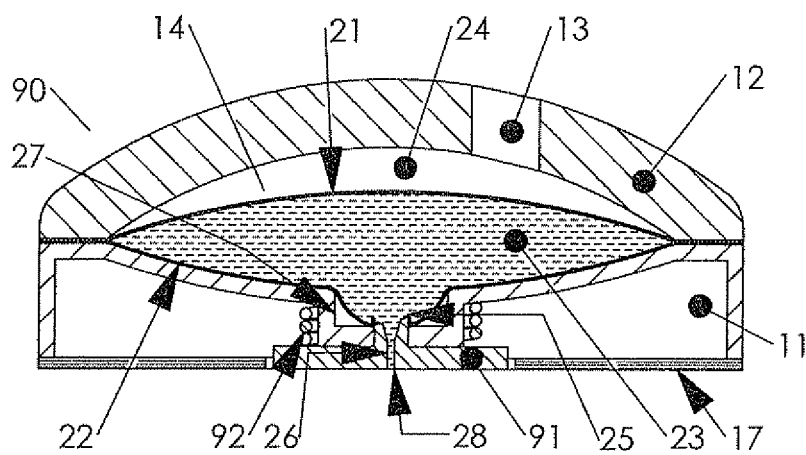

Referring now to FIG. 9, a further preferred embodiment 90 of the present invention is demonstrated which incorporates a safety feature that prevent accidental activation when the apparatus is not attached firmly to the skin. One of the risks with needleless injector is that the liquid jets can cut in the skin if not directed in perpendicular to the skin causing a serious wound. The embodiment 90 comprises the basic elements of embodiment 10, and in addition comprises a key 91. The key 91 comprises the fluid conduit 26, the rupturing member at one end of the fluid conduit 26 proximal to the pouch 14, and an administrating orifice 28 at the other end of the fluid conduit 26 emerging from surface 92 which is designated to hold against the skin. The arrangement is such that the key 91 can move toward and away from the apparatus whereby the rupturing member 25 to move toward and away from the pouch 14 respectively. The coupling member 91 maintain a fluid tight seal with the recess 27 such that upon rupture of the pouch 14, the deliverable fluid 23 is limited to expel through the fluid conduit 26 upon rupturing. The coupling member 91 is biased to a position distant from the pouch (via a spring or other biasing means) 14 in which position the rupturing member 25 can not reach the pouch 14 and a rupturing of the pouch 14 can not occur. When the apparatus 90 is pressed against the target surface, the coupling member 91 is forced to move toward the pouch to a position—shown in FIG. 9b—where the rupturing member 25 and the pouch 14 can get in contact upon the pressurizing the pouch 14. Upon firmly pressing the base against the skin the penetration member is displaced into the base against the spring force, in which position the pressurized pouch can contact the rupturing member and activate—see FIGS. 9b and 9c for the different steps in this process. In a yet further embodiment the apparatus is a hand held device which is not to be adhered or otherwise remain on the skin, and therefore it may be advantageous to change the procedure sequence such that pressurizing of the reservoir occurs prior to positioning the device on the skin, and therefore the administration will occur immediately after positioning the device on the skin.

Figure 10A:
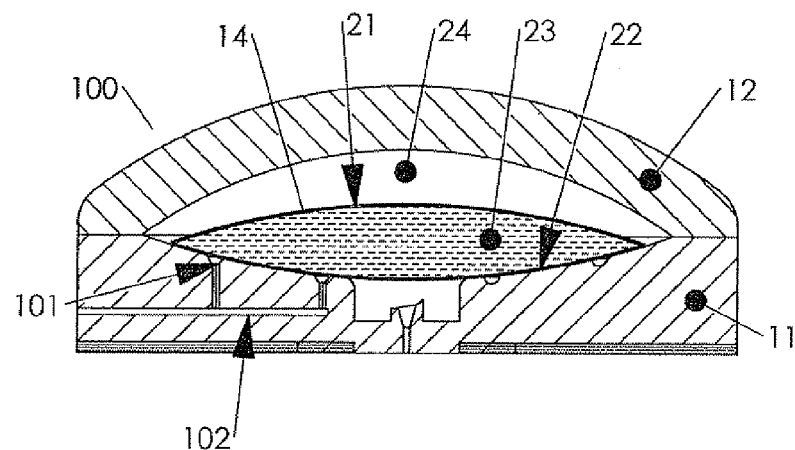
FIG. 10 present a further preferred embodiment of the present invention where the reservoir is independent from the pressure chamber construction.
Figure 10B:
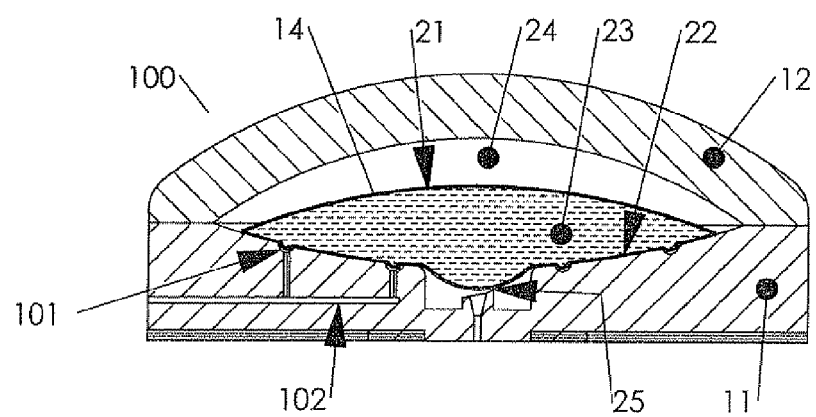
Figure 11A:
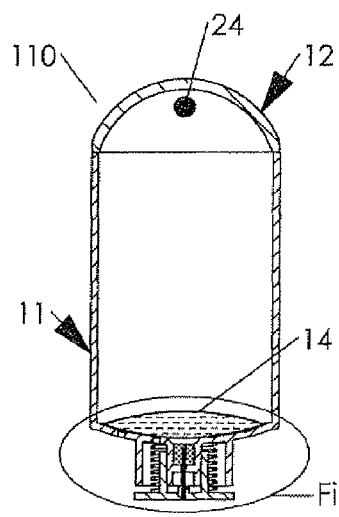
FIG. 11 present a hand held embodiment of the present invention.
Figure 11B:
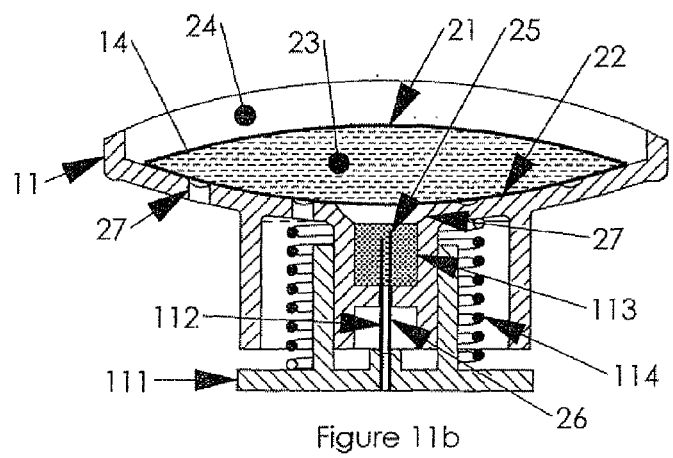
Figure 11C:
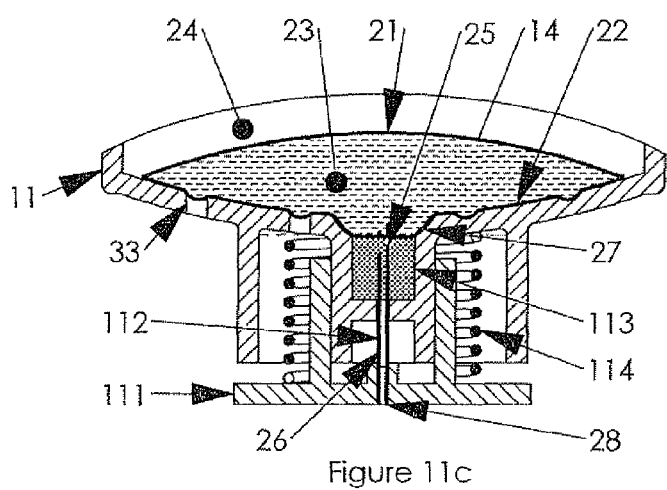
Figure 11D:
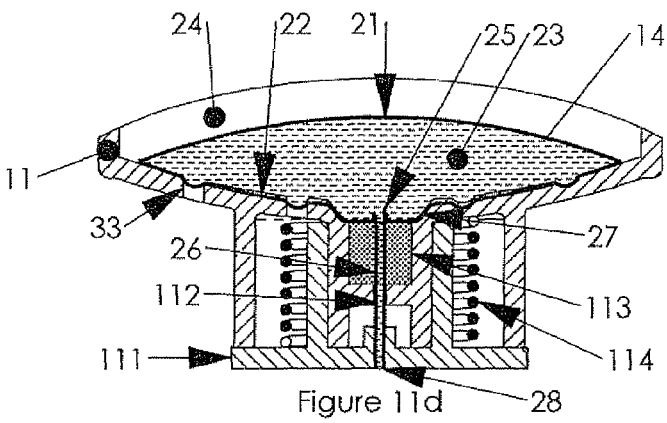

Referring now to FIG. 10 a further preferred embodiment of the present invention in demonstrated in which the pouch 14 is not clamped between the cover 12 and the base 11. Instead the cover 12 is sealed directly to the housing 11, and the pouch 14 is accommodated on the base 11. The pouch 14 is preferably attached to the housing via adhesive back, welding, glue or by the pressure differences between the two sides of the $1^{st}$ wall 22—resulting from having the fluid 23 pressurized on one side and the ventilation holes and channels 101 on the other side—or by any other means known in the art.

FIG. 10 b demonstrates how the pressurizing the pouch 14 causes the wall 22 to be sucked onto the channels 101 in the housing 11.

Referring now to FIG. 11 a further preferred embodiment 110 of the present invention is demonstrated in a form of a hand held apparatus 110. The cover 14 is shaped for a comfortable grip of the hand. The apparatus 110 comprises a key 111 similar in function to the key 91 of embodiment 90, but differ from key 91 by that it comprises a separate rigid canula portion, fixed to the key's base, providing the fluid conduit 26 and its end proximate to the pouch being the rupturing member 25. The canula can be made from various materials including rigid plastic or stainless and it can be incorporated to the key base by various methods including molding, co-molding, insert-molding, any welding technique, gluing, press fit, or any other means know in the art. The key 91 of embodiment 90 which can move toward and away from the pouch 14, manipulating the rupturing member 25 toward and away from the rupturable portion of the $1^{st}$ wall 22 respectively. In the rest position demonstrated in FIG. 11b the spring 114 is forcing the key away from the pouch 14. The tip of the needle 25 proximate to the pouch 14—being the rupturing member is located inside a septum part 113. FIG. 1c demonstrates the apparatus 110 when the pouch is pressurized (the armed position of the apparatus 110) showing the $1^{st}$ wall 22 of the pouch 14 being stretched into recess 27 to lean against the septum 113. The air presented in the recess 27 in the rest position has been ventilated from ventilation channels around the septum (not shown). FIG. 1d demonstrate the apparatus 110 at the activated position. By leaning the sliding part against the skin the sliding part 111 retract causing the needle 112 to extend through the septum and rupture the pouch 14 causing the release of the deliverable fluid to the administration means 28. It will be obvious to those skilled in the art that with certain pressurizing devices the procedure sequence can be altered such that the device is first pressed against the skin following by activation of the pressurizing device. The advantage of incorporating the septum 113 is that it provides and excellent sealing around the canula 112 in a simple fashion. It will be obvious to those skilled in the art that further activation means can be added such as a trigger knob that will activate the rupturing. Further safety features can be added such as a safety catch that prevents the sliding part from moving until it has been removed. Upon release of the firm hold of the apparatus 110 on to the skin, the sliding part 111 retracts away from the pouch pulling the needle away from the part. In a further embodiment a locking mechanism locks the sliding part 111 in the retracted position preventing abuse of the remaining fluid in the patch.

Referring to FIG. 12 a further preferred embodiment 120 of the invention is demonstrated. Apparatus 120 is a hand held apparatus having the slider arrangement similar to embodiment 110. FIGS. 12a and 12b demonstrates the apparatus 120 in the rest position enclosed in a sterile package. The $2^{nd}$ wall 21 of the pouch 14 serves as a portion of the sterility package, with sealed peripheral to the sterility blister package 123. The blister 123 is removed prior to administration. In one embodiment the apparatus 120 is intended for a single use and the cover 12 (not shown) can be ready assembled to the base such that the edges of the wall 21 and the blister 123 remains connected in a sealed fashion. In another single use embodiment the cover 12 can be supplied separately from the apparatus and mounted on the base by the user. This can be advantageous for various reasons: a) if the cover can damage the sterility of the package, b) if the pouch 14 has to be filled before use, c) or if the reservoir comprises more than one compartment and an access is required to manipulate said compartment to merge and mix as described in the text of FIG. 11. In a yet another preferred embodiment the cover is part of a multi-use system and it is connected to the apparatus 120 prior to use. The $2^{nd}$ wall 22 confines a septum assembly which comprises of a compressed rubber portion 121 and a compressing rigid ring. In the rest position the rupturing member 25 is set a distant from the wall 22.

FIG. 12c demonstrated the apparatus when the cover is assembled in a sealed fashion to the base 11, and when the pouch 14 is pressurized. FIGS. 12d and 12e demonstrated the apparatus in the activated position. The sliding part 111 is pressed against the skin (not shown) forcing it to travel toward the pouch causing the rupturing member 25 to penetrate the wall 25 and go through the rubber portion 121 of the septum 121 and fluid-connect the deliverable fluid 23 with the fluid conduit 26. Upon releasing the firm hold force of the apparatus against the skin, the sliding part 111 retracts and the rupturing member disengage from the pouch.

In a further embodiment a yet another rupture-control mechanism is implemented. In this embodiment the initial position of the septum assembly and its confining portion of wall 22 is outside or partly outside recess 27, and it is biased from entering the recess by a spring, friction or other biasing means known in the art. In this position the septum is not accessible by the rupturing means 25. Upon pressurizing the reservoir 14 to a defined threshold pressure the septum assembly penetrates the recess 27, allowing the rupturing member 25 to rupture the reservoir 14.

FIG. 12f demonstrates a local view of a further configuration of the sliding part 111 where the administration device are micro-needles 25. The micro-needles are in fluid connection with the needle 112. It is emphasized here that every one of the embodiments presented for the present invention could be adopted to receive various administration means including needless orifice injector, micro-needle or micro-needles, needle or needles or other administration means known in the art.

Referring now to FIG. 13 a further preferred embodiment 130 is demonstrated where the administration device is a needle with a self insertion mechanism. FIG. 3a demonstrates a perspective view of embodiment 130 showing the cover 12 and a pressurizing device 131. The bottom surface of the apparatus 130 comprise an adhesive layer for adhering the apparatus 130 to the skin. FIG. 3b demonstrates an exploded view of embodiment 130 which comprises a pressurizing device 131 attached to the cover 12; and pouch 14 accommodated on moving plate 31; a needle 51 is accommodated in a guiding spring 138; and an adhesive layer for attaching the apparatus 130 to the body. The pressurizing device 131 is a prefabricated assembly comprising a first film wall 132 and a second film wall 133 (not visible) joined in a pattern such that two separate compartments are formed containing a first reagent and a second reagent, which upon interaction of said reagents will generate pressurized gas. The cover 12 comprises an opening 139 for receiving pressurized gas generated by the pressurizing means 131.

Referring now to FIG. 13c a section view of embodiment 130 is demonstrated in the rest position. The two compartments of the pressurizing device 131 are clearly visible where the first compartment 134 contains a liquid ingredient 136 and the second compartment 135 contains granules of solid ingredients. In the rest position the content of the first compartment 134 and the second compartment 136 are isolated from each other by a sealed joint between the walls 132 and 133, such that interaction between the ingredients 135 and 137 is prevented, therefore pressure chamber 24 is not pressurized. Chamber 24 is defined by the cover 12 and moving plate 31. Moving plate 31 comprises a flat area for accommodating the pouch 14, having a central recess for receiving septum 113 and circumferential flexible section in a form of a bellows, said bellows allows an axial displacement of the flat central surface of the bellows under the presence of force. The moving plate 31 is made from a material having substantial flexibility to support the bellows action such as plastic films, foils, thin sheet of plastic or metal, molded or co-molded polymers (such that the bellow is flexible but the flat area is rigid. The peripheral of the moving plate 31 is joined with the cover 12 in a sealed fashion to form the pressure chamber 24.

The needle 51 is fixed to the center of a dome sheet metal spring 138 which bias the needle against septum 113. The force applied by the spring is not sufficient for the needle to penetrate the septum but merely locate the sharp tip of the needle 51 against the septum 113.

Referring now to FIG. 13d, a section view of the apparatus of embodiment 130 is demonstrated in the activated position. By pressing on the first wall 132 of the pressurizing device 131 the acidic solution 136 is pressurized thus causing the sealed joint between compartment 134 and 136 to separate and the reagents 135 and 137 to merge and mix, which in return initiate a gas generating interaction between the reagents. The pressurizing device 131 has to produce sufficient gas to operate the apparatus 130, including insertion of needle 51 to a subject, rupturing the reservoir 14, and delivering the deliverable fluids to the subject. In one embodiment the interaction between substance 137 and 135 is a chemical reaction. In one embodiment the first reagent 36 is citric acid solution and the second reagent 37 is sodium-bicarbonate is solid form which upon chemical reaction yields carbon-dioxide gas (and salt). Carbon-dioxide saturation at room temperature is in the range of 10 MPA which allows substantial pressure buildup in the pressure chamber 24 by small quantities of reagents. When reacted with an citric acid, one molecule of sodium bicarbonate (84 grams) produces one molecule of carbon dioxide therefore one mole of the bicarbonate will produce 1 mole of carbon dioxide, which in room temperature will occupy approximately (depending on the ambient pressure) 24 Liters. For needle administration, depending on the viscosity of the deliverable substance and the desired delivery rate, a good pressure delivery approximate is 2 bars. Assuming that at the end of the administration period the volume of the pressure chamber 24 is about 10 cc (0.01 Liter), it will require approximately 0.07 gram $$\left[ \frac{0.01_{Liter}}{24_{Liter/mole*bar}} * 2bar * 84_{gram/mole} \right]$$

of sodium-bicarbonate to fully deliver the deliverable fluid (in room temperature).

The gas generated in the pressurizing device 131 flows into the pressure chamber 24 through opening 139 in the cover 12. In one embodiment the second wall 133 of the pressurizing device 131 comprise a weak section which is aligned with opening 139 of the cover 12, said weak area will rupture under the presence of pressure in the combined compartment (134+ 135). In another embodiment the second wall 133 comprises a porousive section, or a mesh, or a hydrophobic mesh section aligned with the opening 139 such that pressurized fluid can penetrate the pressure chamber 24.

The bellows of the moving plate 31 is set to collapse under a predefined desired pressure such to achieve a) enough force for insertion of the needle 51 to the subject and rupture of the reservoir 14, and yet allow enough pressure at the end of the moving plate 31 displacement to deliver the deliverable fluid 23. Assuming an ideal gas the pressure in the pressure chamber will drop during the moving plate collapse in inverse relation to the increase of the pressure chamber volume. A good minimal force approximate for the insertion of 0.5 mm diameter needle is 10 grams which is an insignificant value for the moving plate (of few square centimeter spread) to achieve under 2 bar. The reservoir 14 rupture force value is set to be higher than the skin penetration force by a desired safety factor.

As the moving plate displaces downward, septum 113 urge the needle into the skin. Guide spring 138 guides the needle motion from the concealed position to the extended position where the needle is inserted into the skin of the subject. At this point the guide spring 138 reaches an abutment defining the end of the needle 51 travel, at which point the second end of the needle 51 penetrated the septum and rupture the reservoir 14 thereby administrating the fluid. At the end of the administration procedure the pressure chamber 24 can be depressurized prior to removing the apparatus 130 from the skin, thereby causing the bellows to extend and retract the needle back into a concealed position in the apparatus.

One mean for depressurizing the pressure chamber 24 is by puncturing the cover 12. In one embodiment a permanent ventilation opening in the cover 12 allows the gas to expel from the pressure 24 at a lower rate than the gas generating rate of the pressurizing device. One the gas generating reaction in the pressurizing device 131 is slowing down or stops, the ventilation hole will cause the pressure chamber to depressurize. In yet another embodiment after the administration of the deliverable fluid has been completed the pressure in the pressure chamber keeps rising until it rupture a predefined weakened section in the wails of the pressure chamber 12 or a joint between two portions of the walls.

In one embodiment a depressurizing valve arrangement is such that a portion of the valve leans against the skin of the subject when the apparatus 130 is attached to the skin, keeping the valve shut. As soon as the apparatus 130 is removed from the skin the valve opens and depressurizes the pressure chamber. In yet another embodiment the depressurizing means is activated by a controlled chemical reaction controlled by the pressurizing device 131.

In one embodiment of apparatus 130 the reservoir 14 comprises more than one compartment for sequential delivery of the content of at least two compartments and/or for mixing of the content of at least two compartments prior delivery, as described in the description of embodiment 70. In one embodiment a first compartment and a second compartment of the reservoir 14 are separated by a seperateable sealed joint, and the arrangement is such that (as in embodiment, 70) upon pressurizing the pressure chamber 24 to a first pressure value, said seperateable joint will separate and the deliverable ingredients of said two compartments will mix. A presence of a second pressure value in the pressure chamber 24, higher than said first pressure value, will cause the displacement of moving plate and thereupon the insertion of the needle to the skin of the subject, the rupture of the reservoir 14 and the delivery of the mixed ingredients of said two compartments to the subject. The embodiment described here above provides means for automatically administrating of at least two substances that has been stored separately until the activation of the delivery device. For some indications it is preferable to allow some time for the ingredients to mix prior to administration, in which case a defined time delay is required from the moment that said first pressure value is obtained in the pressure chamber 24 (which cause said compartments to merge)

to the time that said second pressure value is obtained in the pressure chamber 24. In some embodiments said delay is provided by the regime of the pressure generating rate of the pressurizing device 131. In one embodiment a flow restrictor located between the pressurizing device 131 and the pressure cell 24 controls the rate in which the generated gas penetrates the pressure chamber 24 thereby causing a gradual pressure building in the pressure chamber 24 therefore providing a time delay between said first and said second pressure values.

In another embodiment the gradual pressure building in the pressure chamber 24 is due to a slow chemical reaction between the ingredients. In yet another embodiment the chemical reaction rate is controlled by delaying means such as micro-encapsulation of one reagent which is in a solid form, or by any other chemical reaction control mechanisms know in the art. In yet another embodiment two pressure devices are activated simultaneously—a first pressure device instantly provides the first pressure value and the second pressurizing device provides the second pressure value in a delayed time. It will be obvious to those skilled in the art that other mechanisms are suitable for creating a time delay between said first pressure value and said second pressure value. The apparatus described above is composed from simple and inexpensive parts and assemblies yet provides a complex and comprehensive procedure where upon a single activation it will mix separately stored deliverable ingredients; allow time for the ingredients to mix; insert an administration needle; rupture a prefilled sterile reservoir; administrate the substance to a subject; retract the administration needle to prevent accidental injuries or abuse; disconnect the administration needle from the reservoir to further prevent abuse.

It will be obvious to those skilled in the art that several components of embodiment 130 could be integrated into fewer components. For example the second wall 133 of the pressurizing device 131 can be provided by the cover 12, or in another example the flat portion of the moving plate 31 provides a portion of the wall of the reservoir 14.

In one embodiment the pressurizing device assembly contains just one reagent which interacts with a second reagent that present in the pressure chamber 24. In one embodiment said second reagent is air.

Figure 14A:
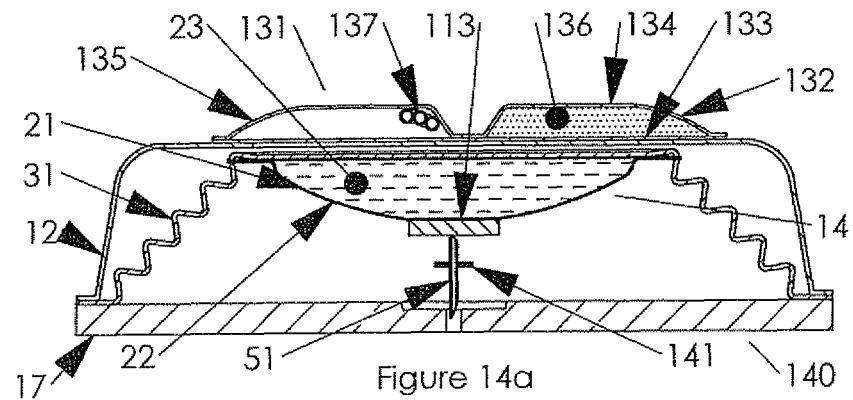
FIG. 14 demonstrates a further preferred embodiment of the device of the present invention comprising a hypodermic needle administration device.

Referring to FIG. 14, a further preferred embodiment 140 is demonstrated. Embodiment 140 is fairly similar in construction to embodiment 130 and is presented to emphasis detail variations from embodiment 130. In embodiment 140 the guiding spring 138 of embodiment 130 is eliminated. In the rest position demonstrated in FIG. 14*a* the needle is retained in a concealed position in the apparatus by having the rupturing end of said needle 51 partially penetrated into septum 113 providing a friction connection, and the administration end of said needle 51 is partially penetrated into a central opening of adhesive pad 17. The friction force between the needle 51 and the septum 113 is greater than the force required for the needle to penetrate the subject's skin. The needle comprise a lateral protrusion 141 located along its wall. It is also noted from FIG. 14*a* that unlike embodiment 130 the reservoir 14 is not located in the pressure chamber, but instead it is accommodated on the second side of the moving plate 31, external to the pressure chamber 24. Therefore the pressure in chamber 24 does not directly pressurize the deliverable fluid 23.

Figure 14B:
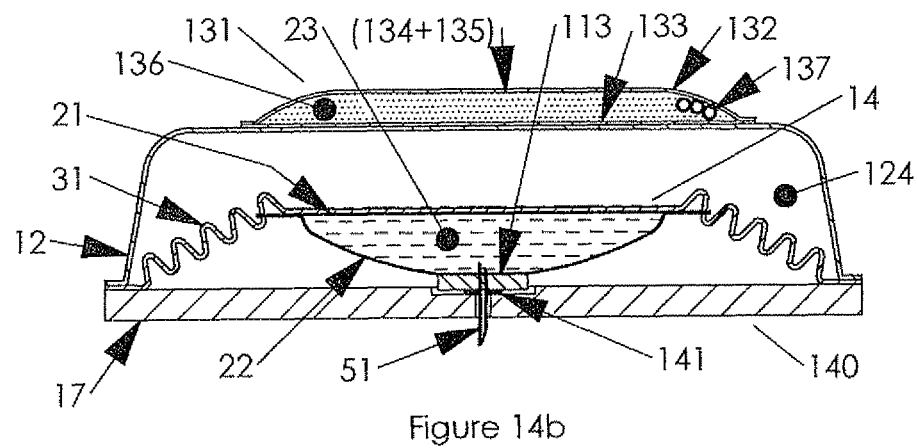

FIG. 14*b* demonstrates an intermediate position of the pressurizing stage of the apparatus 140 in which the pressure chamber is partially pressurized and applies force to moving plate 31 such that urging the bellows section of the moving plate to partially collapse, and the moving plate 31 to be partly displaced downward. In said partially displaced position of the moving plate 31, the needle 51 has already been inserted to the skin of the patient until the lateral protrusion 141 has reached an abutment, there after the needle is urged to penetrate reservoir 14 establishing fluid communication between the body of the subject and the deliverable fluid. The pressure in the pressure chamber 24 does not directly affect the pressure in the reservoir 14. Instead the reservoir 14 is pressurized by it being squeezed between the moving plate 31 and the pad 17 until the deliverable fluid has been almost entirely delivered. Embodiment 140 provides a more controlled means for administrating the deliverable fluid as the reservoir 14 is not pre-pressurized. Upon depressurizing the pressure chamber 14 the moving plate will retract pulling the needle 51 back to a concealed position in the apparatus 140. In one embodiment the pressure chamber 24 is depressurized by puncturing the moving plate 31. In this embodiment a sharp puncturing member is located on the pad 17 such that when the bellows section of the moving plate 31 has completed its downward travel it presses against said sharp puncturing membrane and puncture. The design is such that the puncturing will occur after the administration has been completed. In another embodiment a depressurizing valve is implemented which is activated when the moving plate has reached its maximum downward position. In one embodiment a pressure control arrangement is incorporated such that excess pressure is released from the pressure chamber 24 or the pressurizing device 131 thus keeping a relatively constant propelling pressure during administration.

In yet another embodiment the depressurizing action is noticeable to a person (visual or sound) and signals to remove the apparatus from the skin.

It will be obvious to those skilled in the art that a similar construction to those of embodiments 130 and 140 can be adapted to a needleless or micro-needles administration configuration of the present invention.

The apparatus of the present invention can be miniaturized such that one or more than one apparatus can fit in a bandage.

Referring to FIG. 15, a further preferred embodiment 150 of the present invention is demonstrated. FIG. 15*a* shows a perspective view of a hand held device 150 comprising a body 151 and a sliding button 152 disposed in a groove 158. The body 151 further comprises an opening 156 for the needle 153 (not shown) to exit the body 1511. The groove 158 further comprises a widening zone 158'. A film reservoir 14 is disposed on the external side of the wall of the body 151 inline with the groover 158. The reservoir 14 comprises a first compartment 23 and a second compartment 71 separated by a rupturable seal 62. FIG. 15*b* shows an upper view of the device 150 to provide general orientation of the proceeding section views FIGS. 15*c*, 15*d*, and 15*e*, along section line A-A.

FIG. 15*c* demonstrates a section view of the device 15 at the Rest position. The button 152 is locates in a retracted position. The button 152 comprises a downward rib 157 which is accommodated in the groove 158. The button 152 further comprises two lateral prolongations 159 from the rib 157 in perpendicular direction to the rib 157 and the groove 158, said prolongation 159 prevent the rib 157 to exit the groove 158 thereby preventing a rotational movement of the button 12. The button 152 is therefore limited to linear motion along the groove 158. At this position the reservoir 14 is easily accessed with a finger. By pressing the first compartment 23 with a finger the fluid in the compartment pressurizes and as a result the rupturable seal 62 is ruptured causing the content of the first compartment 23 and the second compartment 71 to merge. A rubber septum 113 is accommodated in an opening in the body 151 under the reservoir 14. The needle 153 is concealed in the body 151. The needle comprises a distal end 153' for penetrating a tissue of a subject, and a proximal end 153" for rupturing the reservoir 14, and from which the fluid enter the needle to be delivered at the distal end 153'. The needle is attached to a needle hub 154 which can travel along the body 151. The needle hub 154 is connected to the button 152 such that they can travel together along the body 151.

Referring now to FIG. 15d, the device 1500 is shown after compartment 71 has been merged with compartment 23 of the reservoir 14, and the button 152 has been advanced along groove 158 toward the reservoir 14 by pushing it with a finger. At this position of the button 152, the prolongations 159 align with the widening 158' of the groove 158, allowing the button to rotate. The needle hub 154 has advanced with the button 152 causing the distal end 153' of the needle 153 to extend out of the body through opening 156.

FIG. 15e demonstrated the administration position of the device 150. The needle is now inserted to the tissue of a subject (not shown). By further forcing the button 152 toward the reservoir the button 152 rotates and depresses the reservoir 14 causing the first wall of the reservoir to stretch down and the septum 113 along. The displacement of the septum 113 and the wall 22 causes the proximal end of the needle 153' to rupture and penetrate the reservoir, forming fluid communication between the fluid in the reservoir and the target tissue.

Referring now to FIG. 16 a further preferred embodiment of the present invention is demonstrated. FIG. 16a demonstrates a perspective view of the device 160 which is mostly similar with the device 150 of FIG. 15, with the exception that a groove 165 in the upper wall of the body 161 having a U shape defines a cantilever surface 164 on which the reservoir is located. The reservoir can be welded or glued to the cantilever surface or attached by any other means known in the art. FIG. 16b shows an upper view of the device 160 providing general orientation of the proceeding section views FIGS. 16c, 16d, and 16e, along section line A-A.

FIG. 16 demonstrates a section view of the device 160 in the Rest position. The body 161 comprises a concaved recess 162 located under the reservoir 14 having a thin wall section 163 at its center. The function of the button 152 and the operation of the needle 153 and hub 154 are similar to that in FIG. 15.

Figure 16A:
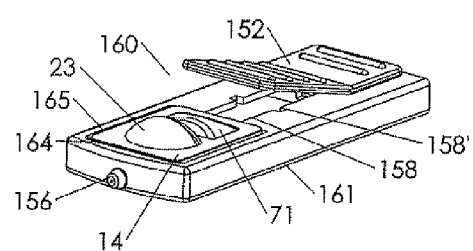
Figure 16B:
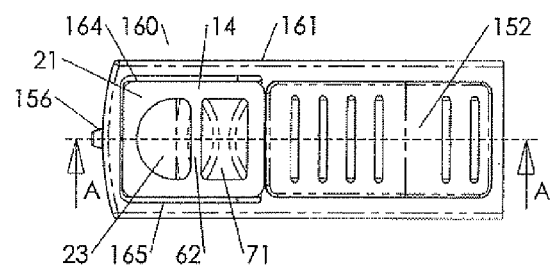
Figure 16C:
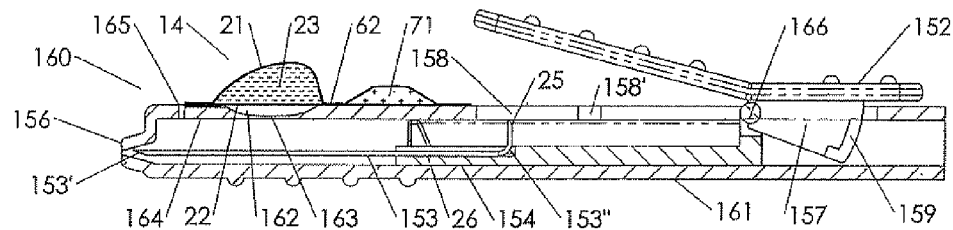
Figure 16D:
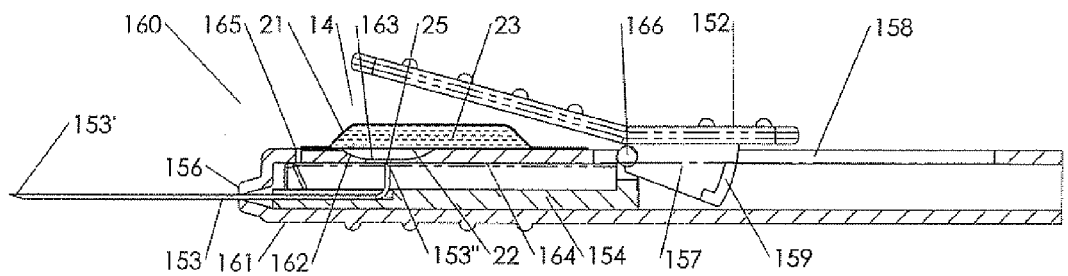

FIG. 16d shows the device after the compartments of the reservoir 14 has been merged, the button 152 is advanced with a finger toward the reservoir 14, and the needle extends from the body 161.

Figure 16E:
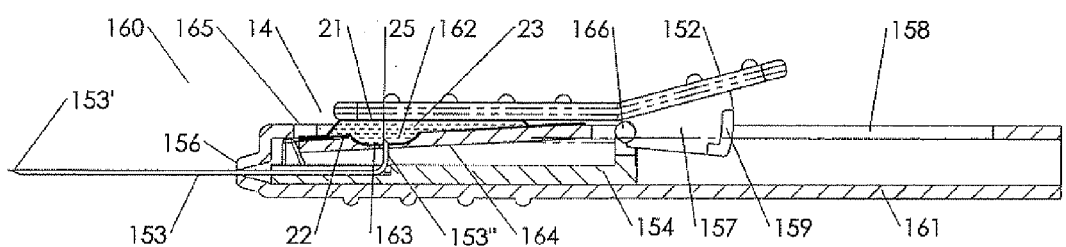

FIG. 16e demonstrates the device 161 at the administration position where the button is further forced with a finger toward the reservoir 14 thereby compressing the reservoir and stretching the first wall 22 to adopt the form of the recess 162. The trapped air in the recess 162 is evacuated through a channel 167 in the body 161, as the stretching portion of the first wall 22 fills the cavity 162. The reservoir forces the cantilever surface down toward the proximal end of the needle 153" until the sharp rupturing end 25 of the needle 153 penetrates the wall 163 and ruptures the first wall 22 of the reservoir 14, thereby forming fluid communication through the needle 153 to the target tissue.

Referring now to FIG. 17 a further preferred embodiment of the present invention is demonstrated. FIG. 17a demonstrates a perspective view of the device 170 which is mostly similar with the device 150 of FIG. 15. FIG. 17b shows an upper view of the device 170 providing general orientation of the proceeding section views FIGS. 17c, 17d, and 17e, along section line A-A.

FIG. 17c demonstrates a section view of the device 170 at the rest position. The body 171 comprises a concaved recess 172 which at its center a rupturing member 25 is located. A cavity 173 is located at the center of the recess 172 having a thin wall 174 facing the hooked distal 153" of the needle 153. The function of the button and the operation of the needle 153 and hub 154 are mostly similar to those of device 150 of FIG. 15.

FIG. 17d shows the device after the compartments of the reservoir 14 has been merged, the button 152 is advanced with a finger toward the reservoir 14, and the distal end of the needle extends from the body 171. The proximal end of the needle 153" pierced the thin wall 174 of the cavity 173, establishing fluid communication between the recesses 172 and the needle 153.

FIG. 17e demonstrated the administration position of the device 170. The needle is now inserted to the tissue of a subject (not shown). By further forcing the button 152 toward the reservoir 14 the button 152 rotates and depress the reservoir 14 causing the first wall of the reservoir 22 to stretch down and reach the rupturing member 25 thereby causing the wall 22 to rupture establishing a fluid communication between the reservoir and the target tissue through the needle 153. The displacement of the septum 113 and the wall 22 causes the proximal end of the needle 153' to rupture and penetrate the reservoir, forming fluid communication between the fluid in the reservoir and the target tissue.

It will be obvious to those skilled in the art that the scope of the present invention is not limited to the embodiment that have been presented, and in particular that various combinations of details and features from one embodiment are applicable for the other embodiments.

I claim:

1. A drug delivery apparatus for delivering pressurized fluid, comprising:
    a. at least one reservoir forming a sealed package for the fluid and comprising at least one rupturable wall portion;
    b. a reservoir pressurizing device for pressurizing said reservoir;
    c. at least one rupturing member for rupturing said rupturable wall portion;
    d. at least one fluid administration device communicating with said reservoir via a fluid passageway;
    e. a rupture control mechanism preventing rupture of the wall portion below a threshold pressure, whereby:
        when the threshold pressure is reached, said wall portion may become ruptured by said rupturing member allowing the fluid to enter the fluid passageway and be delivered to a destination through said fluid administration device; and
    f. a pressure chamber for use in pressurizing said reservoir, said rupture control mechanism including a resistance mechanism for preventing pressurization of the reservoir before a requisite pressure has been established in said pressure chamber, wherein said resistance mechanism comprises a collapsible spring disposed in said pressure chamber in confronting relationship to said reservoir, said collapsible spring operative to permit gradual pressure build up in said pressure chamber and to thereafter collapse and cause an instantaneous pressure in said reservoir.

2. A drug delivery apparatus according to claim 1 wherein said fluid administration device is selected from a group consisting of one or more needles, one or more microneedles, one or more needleless-injector orifices, a spray nozzle, a dispersion nozzle, and an aerosolizing nozzle.

3. A drug delivery apparatus according to claim 1 including a stopper disposed in said pouch for preventing said rupturing member from further damaging said reservoir as fluid is expelled therefrom.

4. A drug delivery apparatus according to claim 1 wherein said rupture control mechanism includes a resilient member for resisting displacement of said rupturable wall portion toward said rupturing member.

5. A drug delivery apparatus according to claim 1 further comprising a cover and a base, said rupturing member formed integrally with said base.

6. A drug delivery apparatus according to claim 1 wherein said rupture control mechanism comprises a movable plate biased toward the reservoir and movable away from and towards its biased position in response to pressure in the reservoir.

7. A drug delivery apparatus according to claim 1 wherein said administration device has a pointed end that is movably disposed relative to an exterior surface of said delivery device between a retracted position wherein said pointed end is located within said delivery device and an extended position wherein said pointed end projects exteriorly of said delivery device, said pointed end operative to move from the retracted position to the extended position when the threshold pressure is reached, thereby activating said delivery apparatus.

8. A drug delivery apparatus according to claim 1 further comprising a pressure release device allowing controlled release of excess pressure from said pressure chamber.

9. A drug delivery device according to claim 1 further comprising a reservoir pressurizing device utilizing a pressure source selected from a group consisting of an internal or external chemical reaction, a combustion reaction, a pump, a liquid pump, a gas pump, a foot pump, a manual pump, and a syringe pump.

10. A drug delivery apparatus according to claim 1 wherein said reservoir comprises a plurality of compartments.

11. A drug delivery device according to claim 10 wherein said compartments are mixed prior to rupturing of the reservoir.

12. A drug delivery device according to claim 10 wherein the contents of said compartments are delivered sequentially.

13. A drug delivery apparatus according to claim 1 comprising an activation key formed as a coupling member configured for common movement with said rupturing member, said coupling member biased away from said reservoir.

14. A drug delivery device according to claim 1 wherein said fluid administration device includes a fluid conduit that defines said fluid passageway, said delivery device further comprising a non-return valve for preventing back flow into said reservoir.

15. A drug delivery apparatus according to claim 1 wherein said administration device is biased toward the reservoir and is movable away from and towards its biased position, to and from an administration position, by the presence of sufficient pressure in the reservoir.

16. A drug delivery apparatus according to claim 1 wherein said rupturable wall comprises a sealing member which seals around the rupturing member upon rupture.

17. A drug delivery apparatus according to claim 1 including a deliverable ingredient that mixes with the fluid from the reservoir and is delivered with the fluid through the administration device.

18. A drug delivery apparatus for delivering pressurized fluid, comprising:
   a. at least one reservoir forming a sealed package for the fluid and comprising at least one rupturable wall portion;
   b. a reservoir pressurizing device for pressurizing said reservoir;
   c. at least one rupturing member for rupturing said rupturable wall portion;
   d. at least one fluid administration device communicating with said reservoir via a fluid passageway;
   e. a rupture control mechanism preventing rupture of the wall portion below a threshold pressure, whereby:
      when the threshold pressure is reached, said wall portion may become ruptured by said rupturing member allowing the fluid to enter the fluid passageway and be delivered to a destination through said fluid administration device; and
   f. an anti-abuse device to prevent extraction of fluid from the reservoir after administration has been completed.

19. A drug delivery apparatus for delivering pressurized fluid, comprising:
   a. at least one reservoir forming a sealed package for the fluid and comprising at least one rupturable wall portion;
   b. a reservoir pressurizing device for pressurizing said reservoir and operative to produce a pressure profile over time which controls timing of the reservoir's rupture;
   c. at least one rupturing member for rupturing said rupturable wall portion;
   d. at least one fluid administration device communicating with said reservoir via a fluid passageway; and
   e. a rupture control mechanism preventing rupture of the wall portion below a threshold pressure, whereby:
      when the threshold pressure is reached, said wall portion may become ruptured by said rupturing member allowing the fluid to enter the fluid passageway and be delivered to a destination through said fluid administration device.

* * * * *